(12) United States Patent
Leeflang et al.

(10) Patent No.: US 9,192,752 B2
(45) Date of Patent: Nov. 24, 2015

(54) SERIAL VALVES AND HUBS FOR TUBULAR DEVICES AND METHODS FOR MAKING AND USING THEM

(75) Inventors: Stephen A. Leeflang, Sunnyvale, CA (US); Christian S. Eversull, Palo Alto, CA (US)

(73) Assignee: AUST DEVELOPMENT, LLC, Palo Alto, CA (US)

( * ) Notice: Subject to any disclaimer, the term of this patent is extended or adjusted under 35 U.S.C. 154(b) by 1241 days.

(21) Appl. No.: 13/099,341

(22) Filed: May 2, 2011

(65) Prior Publication Data

US 2012/0004622 A1   Jan. 5, 2012

Related U.S. Application Data

(60) Provisional application No. 61/361,487, filed on Jul. 5, 2010.

(51) Int. Cl.
*A61M 25/14*   (2006.01)
*A61M 39/06*   (2006.01)
*A61M 25/00*   (2006.01)

(52) U.S. Cl.
CPC ........... *A61M 39/0606* (2013.01); *A61M 39/06* (2013.01); *A61M 25/0075* (2013.01); *A61M 2039/062* (2013.01); *A61M 2039/064* (2013.01); *A61M 2039/0633* (2013.01); *A61M 2039/0666* (2013.01); *Y10T 29/49405* (2015.01)

(58) Field of Classification Search
CPC ............... A61M 2039/0633; A61M 2039/064; A61M 2039/0646; A61M 2039/0666; A61M 2039/062; A61M 2039/0653; A61M 2039/0626; A61M 2039/266; A61M 2039/0036; A61M 2039/0081; A61M 39/06; A61M 39/0606; A61M 39/0613; A61M 39/045; A61M 39/22; A61B 17/3498
USPC ............................................. 604/167.04, 256
See application file for complete search history.

(56) References Cited

U.S. PATENT DOCUMENTS

| 4,430,081 A | 2/1984 | Timmermans |
|---|---|---|
| 4,512,766 A | 4/1985 | Vailancourt |
| 4,549,879 A | 10/1985 | Groshong |

(Continued)

FOREIGN PATENT DOCUMENTS

| EP | 0198962 A1 | 10/1986 |
|---|---|---|
| GB | 2284452 | 6/1995 |
| WO | 98/00195 A1 | 1/1998 |

*Primary Examiner* — Nicholas Lucchesi
*Assistant Examiner* — Anh Bui
(74) *Attorney, Agent, or Firm* — William A. English; Vista IP Law Group LLP

(57) ABSTRACT

A hub for a sheath, catheter, or other tubular device includes a first hub portion including a first hub lumen sized for receiving a medical device therethrough, and a second hub portion including a second hub lumen, the second hub portion coupled to the first hub portion such that the first and second hub lumens are aligned with one another and the first and second hub portions are spaced apart from one another to define a gap. A valve is secured within the gap between the first and second hub portions that includes a valve passage therethrough, e.g., for accommodating receiving a medical device through the first and second hub lumens into the tubular device, while providing a substantially fluid tight seal. For example, the valve passage may include a bore extending partially from a first end of the valve towards a second end of the valve, and a slit that extends from the end of the bore to the second end of the valve.

18 Claims, 19 Drawing Sheets

(56) References Cited

U.S. PATENT DOCUMENTS

| | | |
|---|---|---|
| 4,960,412 A | 10/1990 | Fink |
| 4,973,319 A | 11/1990 | Melsky |
| 5,000,745 A | 3/1991 | Guest et al. |
| 5,125,904 A | 6/1992 | Lee |
| 5,147,332 A | 9/1992 | Moorehead |
| 5,201,901 A | 4/1993 | Harada et al. |
| 5,250,034 A | 10/1993 | Appling et al. |
| 5,267,966 A | 12/1993 | Paul |
| 5,304,143 A | 4/1994 | Green et al. |
| 5,312,355 A | 5/1994 | Lee |
| 5,441,504 A | 8/1995 | Pohndorf et al. |
| 5,453,095 A | 9/1995 | Davila et al. |
| 5,702,370 A | 12/1997 | Sylvanowicz et al. |
| 5,944,697 A | 8/1999 | Biche |
| 6,290,668 B1 | 9/2001 | Gregory et al. |
| 6,544,247 B1 | 4/2003 | Gardeski et al. |
| 6,712,791 B2 | 3/2004 | Lui et al. |
| 6,808,509 B1 | 10/2004 | Davey |
| 6,966,896 B2 | 11/2005 | Kurth et al. |
| 2001/0000041 A1 | 3/2001 | Selmon et al. |
| 2003/0050604 A1 | 3/2003 | Lui et al. |
| 2007/0293845 A1* | 12/2007 | Leeflang et al. ............ 604/523 |
| 2011/0004223 A1 | 1/2011 | Leeflang et al. |
| 2011/0040260 A1 | 2/2011 | Leeflang et al. |

* cited by examiner

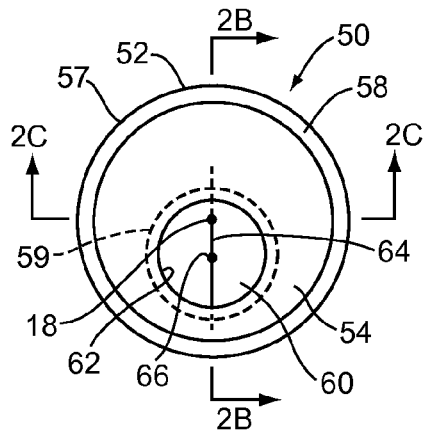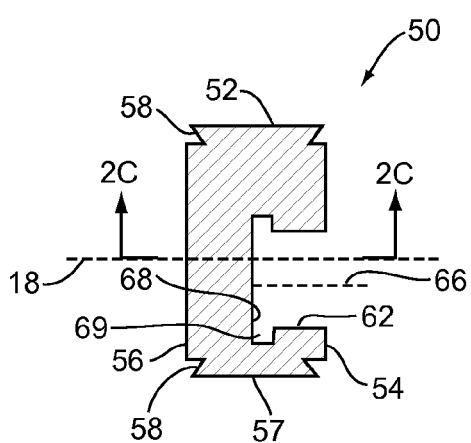
FIG. 2A
FIG. 2B
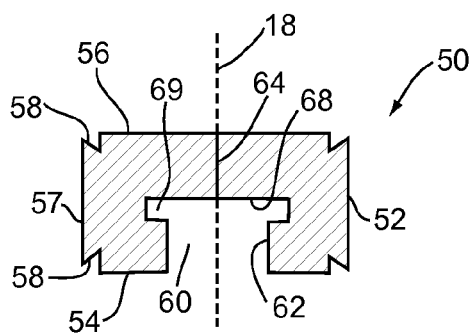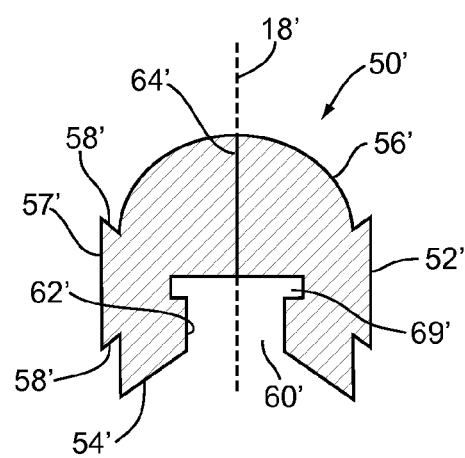
FIG. 2C
FIG. 2D
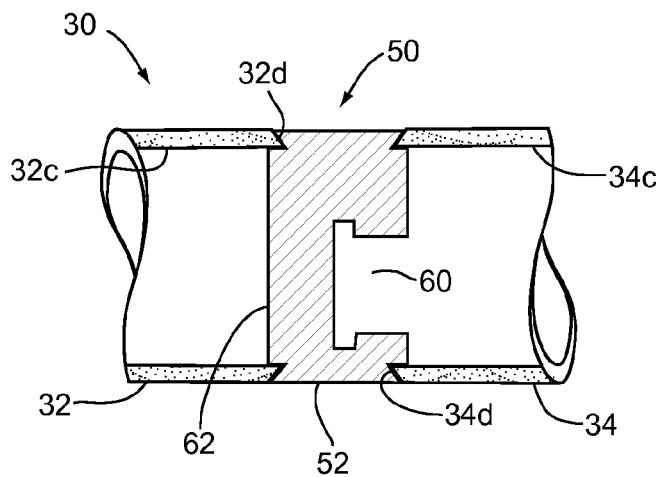
FIG. 3

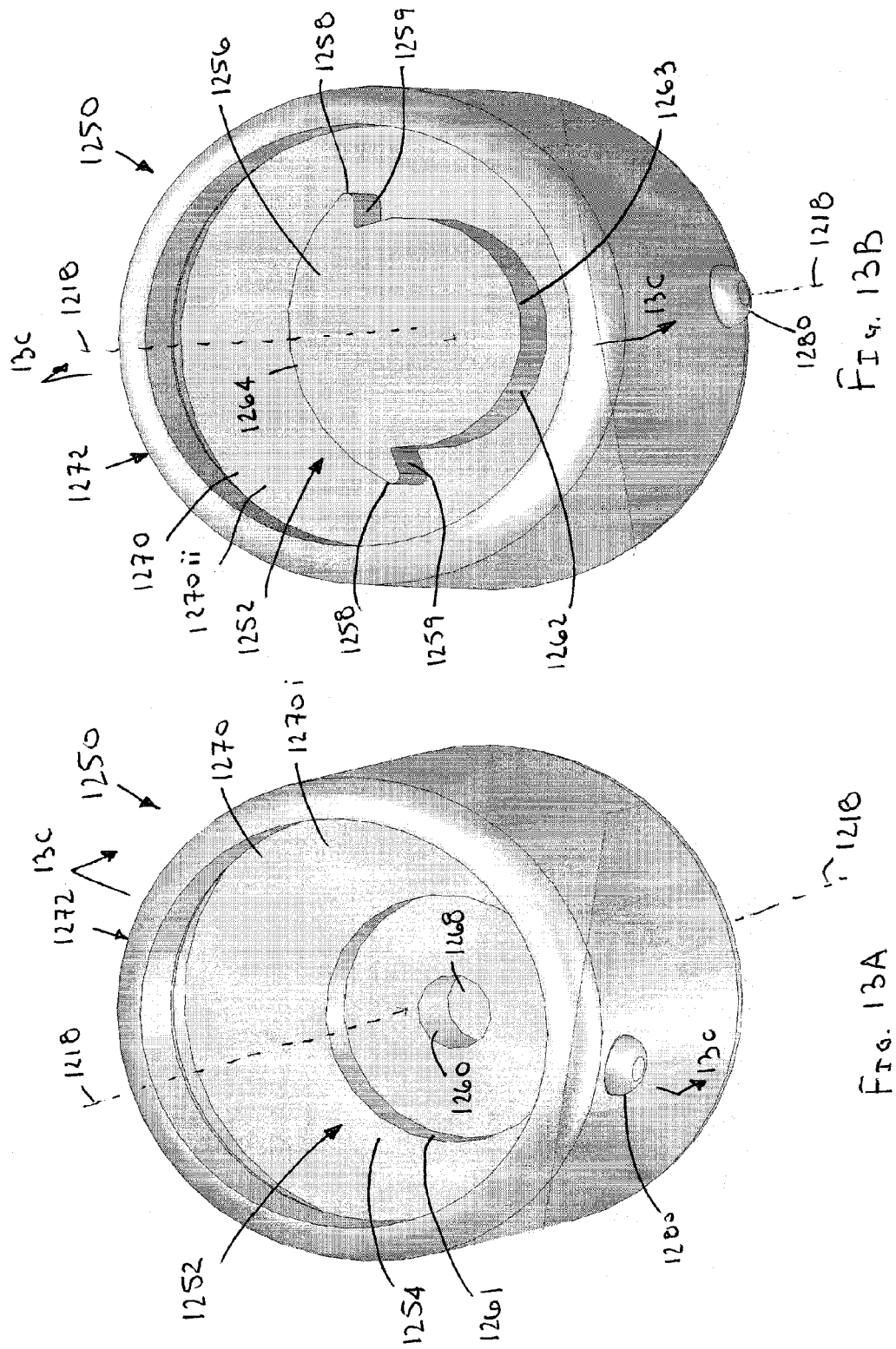

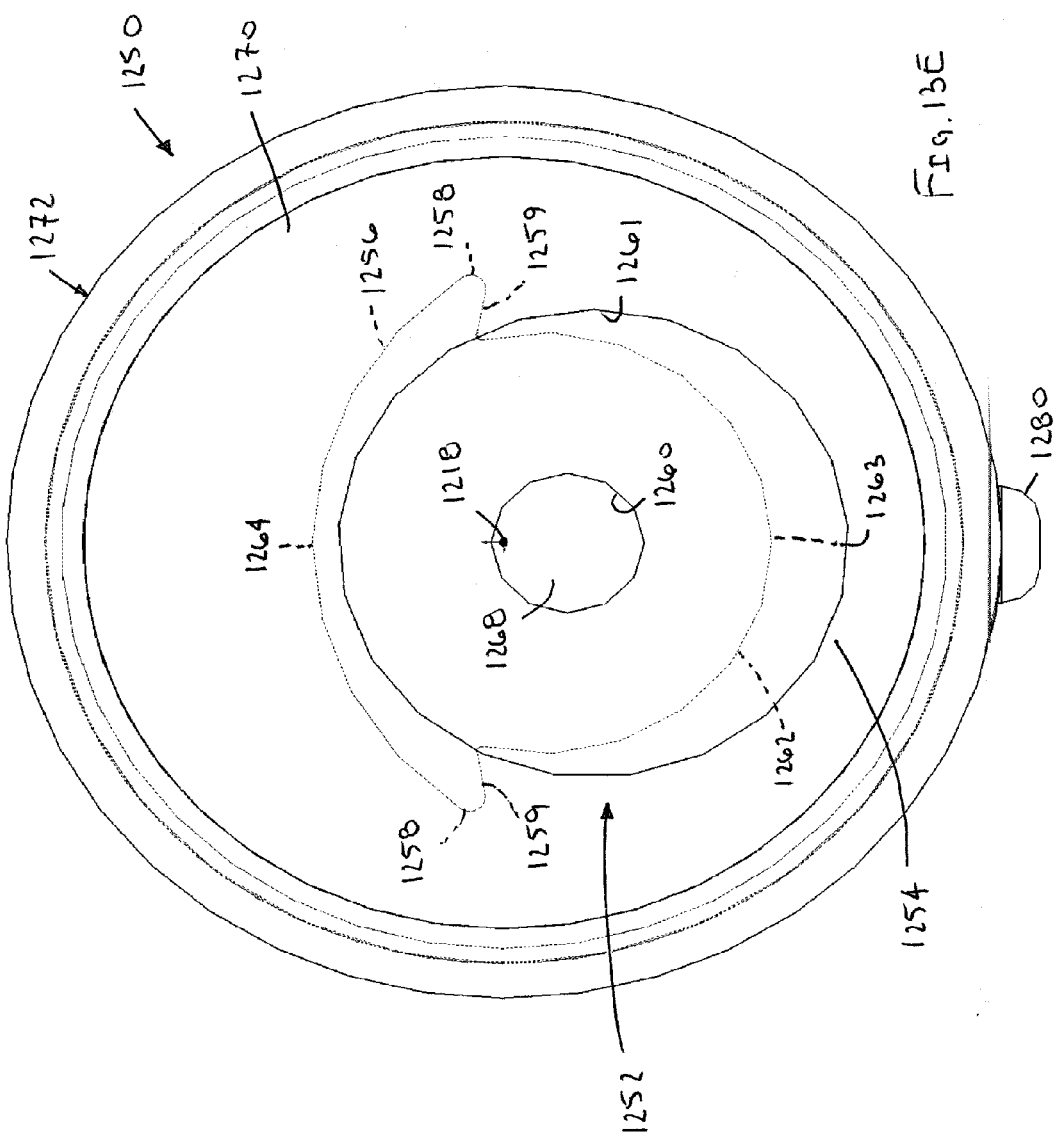

SERIAL VALVES AND HUBS FOR TUBULAR DEVICES AND METHODS FOR MAKING AND USING THEM

This application claims benefit of U.S. provisional application Ser. No. 61/361,487, filed Jul. 5, 2010, the entire disclosure of which is expressly incorporated by reference herein.

FIELD OF THE INVENTION

The present invention relates generally to apparatus and methods for delivering instruments and/or agents during a medical procedure, and, more particularly, to valves and/or hubs for guide sheaths, catheters, and other tubular devices for accessing body lumens and/or for delivering instruments into body lumens of a patient, and to methods for making and using them.

BACKGROUND

There are many medical procedures where a lead, catheter, electrode, and/or other medical device may be implanted into a patient's body cavity, recess, vessel, organ, and/or other body lumen. In many of these procedures, a delivery sheath, guide catheter, or other tubular member may be used to facilitate delivering the medical device, with the tubular member removed after placement of the medical device. Additionally, it may be desirable to provide a substantially fluid tight seal between the delivery sheath, guide catheter, or other tubular member and the lead, catheter, electrode, guidewire, and/or other medical device, e.g., for the purpose of hemostasis, infusion of therapeutic or diagnostic agents, and the like. However, the process of removing the tubular member from around the medical device after the medical device has been placed may be difficult and/or time consuming.

For example, a delivery sheath used to deliver a cardiac lead may not be easily removed from around the lead without disturbing the placement of the lead, which must remain in the patient. Therefore, apparatus that may facilitate the delivery of devices, provide a seal or substantial seal, and/or facilitate removal without substantially disturbing placement of the lead and/or other device may be desirable.

SUMMARY

The present invention is directed generally to apparatus and methods for delivering instruments and/or agents during a medical procedure. More particularly, the present invention is related to valves and/or hubs for guide sheaths, catheters, and other tubular devices for accessing and/or delivering instruments into body lumens of a patient, and to methods for making and using them.

In accordance with one embodiment, a hub is provided for a sheath, catheter, or other tubular device that includes a first hub portion including a first hub lumen sized for receiving a medical device therethrough, and a second hub portion including a second hub lumen, the second hub portion coupled to the first hub portion such that the first and second hub lumens are aligned with one another and the first and second hub portions are spaced apart from one another to define a gap for receiving a valve therein.

In an exemplary embodiment, the second portion may be coupled to the first hub portion by a hub arm. For example, the hub arm may be sufficiently flexible such that the first hub portion may be directed away from the second hub portion to increase a size of the gap to accommodate inserting the valve within the gap and/or that may be resiliently biased to return towards its original shape to capture a valve within the gap. In addition or alternatively, the first and/or second valve portions may include one or more connectors for securing the valve within the gap. Optionally, the hub arm may include a side port including an opening that communicates with the second hub lumen, e.g., for delivering fluid into the second hub lumen.

Optionally, the hub may include a valve secured within the gap between the first and second hub portions. In an exemplary embodiment, the valve may include a valve passage therethrough, e.g., for accommodating receiving a medical device through the first and second hub lumens, while providing a substantially fluid tight seal. For example, the valve passage may include a bore extending partially from a first end of the valve towards a second end of the valve, and a slit that extends from the bore to the second end of the valve. The bore may have a circular or other cross-section, e.g., to accommodate introducing a medical device therethrough, and/or the slit may have opposing slit regions that are biased to close against one another, e.g., to provide a fluid-tight seal, and that are separable to accommodate receiving the medical device introduced through the bore.

In accordance with another embodiment, a valve is provided for a hub of a sheath, catheter, or other tubular device that includes a valve body including a first end, a second end, and an outer surface extending between the first and second ends; and a valve passage extending through the valve body between the first and second ends. In an exemplary embodiment, the valve passage may include a bore extending partially through the valve body from the first end towards the second end, and a slit extending through the valve body from the bore to the second end. The bore may have a circular or other cross-section, e.g., to accommodate introducing a medical device therethrough, and/or the slit may have opposing slit regions that are biased to close against one another, e.g., to provide a fluid-tight seal, and that are separable to accommodate receiving the medical device introduced through the bore. Optionally, the valve passage may include a recess within the bore that has a larger diameter or other cross-section than the bore, e.g., for receiving a lubricant and/or facilitating expansion of the valve when a medical device is inserted through the valve passage.

Optionally, the valve may include one or more connectors for securing the valve body to a hub of a tubular device, e.g., at least one of a groove and a beveled edge on the first end of the valve body. The one or more connectors may extend circumferentially around the first and second ends of the valve body, e.g., similar to corresponding connectors on the hub to which the valve is secured. In alternative embodiments, the connectors may include undersized annular flanges extending from the valve body that are sized to be received in respective openings in a hub, or oversized annular flanges that are sized to be received over respective openings in a hub.

In accordance with still another embodiment, a valve is provided for a hub of a sheath, catheter, or other tubular device that includes a valve body including a first end, a second end, and one or more connectors on the first and second ends for securing the valve body to a hub of a tubular device; and a valve passage extending through the valve body between the first and second ends. The valve passage may include a bore extending partially through the valve body from the first end towards the second end, and a slit extending through the valve body from the bore to the second end. The valve body may be resiliently flexible such that a cross-section of the bore may be increased to accommodate receiving a medical device through the bore that has a cross-section larger than the bore while maintaining a substantially fluid tight seal around the medical device, and/or the slit may include opposing slit regions, e.g., having substantially planar opposing surfaces defining the slit that open to accommodate receiving a medical device through the valve passage yet resiliently close against one another when the medical device is removed to maintain a substantially fluid tight seal through the valve passage.

In accordance with yet another embodiment, a valve is provided for a hub of a sheath, catheter, or other tubular device that includes a valve body including a first end, a second end, and one or more connectors on the first and second ends for securing the valve body to a hub of a tubular device; a valve passage extending through the valve body between the first and second ends, the valve passage including a bore extending partially through the valve body from the first end towards the second end, and a slit extending through the valve body from the bore to the second end; and a lubricant within the bore to reduce friction when a medical device is inserted through the valve passage. The valve body may be resiliently flexible such that a cross-section of the bore may be increased to accommodate receiving a medical device through the bore that has a cross-section larger than the bore while maintaining a substantially fluid tight seal around the medical device, and/or the slit may include opposing slit regions that open to accommodate receiving a medical device through the valve passage yet resiliently close when the medical device is removed to maintain a substantially fluid tight seal through the valve passage.

In an exemplary embodiment, the bore may include a first bore region having a first diameter or other cross-section extending from the first end to an intermediate location in the valve body, and a second bore region at the intermediate location, e.g., at the bottom of the bore, that has a larger diameter or other cross-section than the first bore region, and wherein the lubricant is disposed within the second bore region.

In accordance with still another embodiment, a method is provided for making a valve for a sheath, catheter, or other tubular device that includes forming a valve body including a first end, a second end, and a bore extending partially through the valve body from the first end towards the second end; and inserting an instrument into the bore to create a slit extending from the end of the bore to the second end.

In accordance with yet another embodiment, a method is provided for making a sheath, catheter, or other tubular member that includes forming a hub including a first hub portion including a first hub lumen and a second hub portion including a second hub lumen, the second hub portion coupled to the first hub portion such that the first and second hub lumens are aligned with one another and the first and second hub portions are spaced apart from one another to define a gap; forming a valve body including a valve passage extending therethrough; and securing the valve body within the gap between the first and second hub portions such that the valve passage accommodates receiving a medical device therethrough when the medical device is introduced through the first and second hub lumens of the first and second hub portions while providing a substantially fluid tight seal. In addition, a tubular body may be attached to the second hub portion such that a lumen of the tubular body communicates with the first and second hub lumens.

In accordance with still another embodiment, a method is provided for making a sheath, catheter, or other tubular member that includes forming a handle comprising a first handle portion with a first hub portion including a first hub lumen and a second handle portion with a second hub portion including a second hub lumen, the first and second handle portions coupled together opposite the hub portions such that the first and second hub lumens are aligned with one another and the first and second hub portions are spaced apart from one another to define a gap; selecting a valve body comprising a valve passage extending therethrough; directing the first and second hub portions away from one another to increase a size of the gap; inserting the valve body within the gap between the first and second hub portions; and directing the first and second hub portions towards one another to capture the valve body between the first and second hub portions.

In accordance with yet another embodiment, a method is provided for delivering a medical device into a body lumen within a patient's body. Initially, a distal end of a tubular device may be introduced into the patient's body, the tubular device including a hub on a proximal end thereof that includes a valve secured between a proximal hub portion and a distal hub portion. The distal end of the tubular device may be positioned within a body lumen, and a medical device may be inserted through the proximal hub portion, the valve, and the distal hub portion until a distal end of the medical device is positioned within the body lumen. The proximal hub portion, valve, distal hub portion, and tubular device may be sequentially cut to remove the tubular device from around the medical device while the medical device distal end remains within the body lumen.

In accordance with still another embodiment, a valve is provided for a hub of a sheath, catheter, or other tubular device that includes a valve body including an inlet end, an outlet end, a central longitudinal axis extending between the inlet and outlet ends, and an outer surface extending from the outlet end at least partially towards the inlet end. A bore extends partially through the valve body from the inlet end towards the outlet end, and a slit may extend transversely through the valve body from a first side of the outer surface partially towards an opposite second side of the outer surface, thereby defining a cover in the valve body located between the bore and the outlet end, the cover biased to close the bore and resiliently flexible to open to accommodate an instrument introduced through the bore from the inlet end.

The valve body may include a pair of stops extending from the outer surface adjacent the second side for supporting the cover adjacent a base of the slit. For example, the stops may include stop surfaces, e.g., defining an acute angle with the outer surface adjacent the base of the slit such that the stops resist propagation of the slit to the second side of the outer surface. In an exemplary embodiment, the outer surface of the valve body may define a first curved surface extending circumferentially from the second side partially around the valve body towards the first side, and the stops may include supports extending radially outwardly from the first curved surface to provide stop surfaces defining an acute angle between each stop surface and the first curved surface.

In accordance with yet another embodiment, a method is provided for making a valve for a hub of a sheath, catheter, or other tubular device that includes forming a resiliently flexible valve body including an inlet surface, an outlet surface defining a central longitudinal axis extending therebetween, a circumferential outer surface extending from the outlet surface at least partially towards the inlet surface, a pair of stops extending radially outwardly from the outer surface adjacent the outlet surface, and a bore extending partially through the valve body from the inlet surface towards the outlet surface. A slit may be created that extends transversely through the outer surface from a first side of the outer surface generally opposite the stops partially towards an opposite second side of the outer surface to create a cover in the valve body located between the bore and the outlet end, the cover biased to close the bore and resiliently flexible to open to accommodate an instrument introduced through the bore.

In an exemplary embodiment, the inlet surface, outlet surface, outer surface, stops, and bore may be integrally molded or cast from single body of flexible material. In another embodiment, the inlet surface, outlet surface, outer surface, and stops may be integrally molded or cast from single body of flexible material, and the bore may be subsequently created in the valve body. The slit may be created by directing a cutting element through the first side of the outer surface towards the second side without cutting into the stops such that a base of the slit is located between the stops and the first side.

In accordance with still another embodiment, a valve is provided for a hub of a sheath, catheter, or other tubular device that includes a valve body and a pair of annular flanged connectors. The valve body may include an inlet end, an outlet end, a central longitudinal axis extending between the inlet and outlet ends, a bore extending partially through the valve body from the inlet end towards the outlet end, and a slit at least partially defining a self-closing feature between the bore and the outlet end, the self-closing feature biased to close to substantially seal the bore and resiliently flexible to open to accommodate an instrument introduced through the bore from the inlet end. The flanged connectors may extend substantially parallel to the central axis and/or surround the valve body. For example, the flanged connectors may be sized for being received over spaced apart hub portions of a hub, e.g., for supporting the valve body in a gap between the hub portions.

In one embodiment, the valve body may include an outer surface extending from the outlet end at least partially towards the inlet end, and the slit may extend transversely through the valve body from a first side of the outer surface partially towards an opposite second side of the outer surface. In this embodiment, the self-closing feature may be a cover at least partially defined by the slit, the cover biased to close the bore and resiliently flexible to open to accommodate an instrument introduced through the bore from the inlet end.

In another embodiment, the slit may extend substantially parallel to the central axis through the valve body from the bore to the outlet end. In this embodiment, the self-closing feature may include opposing slit regions at least partially defined by the slit that open to accommodate receiving an instrument through the bore yet resiliently close when the instrument is removed to maintain a substantially fluid tight seal.

Optionally, the flanged connectors may include relatively thin-walled regions between the valve support and the opposite ends to enhance flexibility of the flanged connectors. For example, the thin-walled regions may define annular recesses on inner surfaces of the flanged connectors adjacent the valve body, e.g., sized for receiving adhesive therein to enhance securing the flanged connectors to the hub portions.

In accordance with yet another embodiment, a method is provided for making a valve for a hub of a sheath, catheter, or other tubular device. A valve body and a pair of flanged connectors may be formed, the valve body including an inlet surface, an outlet surface defining a central longitudinal axis extending therebetween, and a bore extending partially through the valve body from the inlet surface towards the outlet surface. The flanged connectors may extend substantially parallel to the central axis and/or may surround the valve body. A slit may be created in the valve body to provide a self-closing feature between the bore and the outlet end, the self-closing feature biased to close to substantially seal the bore and resiliently flexible to open to accommodate an instrument introduced through the bore from the inlet end.

In accordance with still another embodiment, a method is provided for making a sheath, catheter, or other tubular member that includes forming a hub including a first hub portion including a first hub lumen and a second hub portion including a second hub lumen, the second hub portion coupled to the first hub portion such that the first and second hub lumens are aligned with one another and the first and second hub portions are spaced apart from one another to define a gap. A valve may be selected that includes a valve body and a pair of flanged connectors surrounding the valve body, the valve body including a bore extending partially therethrough from an inlet end towards an outlet end and a self-closing feature between the bore and the outlet end. The flanged connectors may be secured over the first and second hub portions such that the valve body is secured within the gap between the first and second hub portions.

In accordance with yet another embodiment, a hub is provided for a sheath, catheter, or other tubular device that includes a first hub portion including a first hub lumen sized for receiving a medical device therethrough and extending concentrically around a longitudinal axis of the hub, a second hub portion including a second hub lumen, the second hub portion coupled to the first hub portion such that the first and second hub lumens are aligned with one another along the longitudinal axis and the first and second hub portions are spaced apart from one another to define a gap, and a valve. The valve may include a valve body and a pair of flanged connectors surrounding the valve body, the flanged connectors received over the first and second hub portions adjacent the gap to secure the valve body within the gap. The valve body may include a valve passage extending therethrough configured to accommodate receiving an instrument therethrough when the instrument is introduced through the first and second hub lumens of the first and second hub portions.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 2A is an end view of an exemplary embodiment of a valve that may be coupled to the hub of FIGS. 1A and 1B.

FIG. 2B is a cross-sectional side view of the valve of FIG. 2A, taken along line 2B-2B.

FIG. 2C is a cross-sectional top view of the valve of FIGS. 2A and 2B, taken along line 2C-2C.

FIG. 2D is a cross-sectional top view of an alternative embodiment of the valve of FIGS. 2A-2C.

FIG. 3 is a cross-sectional detail of the hub of FIGS. 1A and 1B, showing the valve of FIGS. 2A-2C coupled to the hub.

FIGS. 13A and 13B are perspective views of another embodiment of a valve including a central valve body, a valve support surrounding the valve body, and flanges connectors extending from the valve support. FIG. 13A is a view from the inlet end of the valve, and FIG. 13B is a view from the outlet end of the valve.

FIG. 13E is an end view of the valve of FIGS. 13A and 13B, taken from the inlet end.

DETAILED DESCRIPTION OF THE EXEMPLARY EMBODIMENTS

Figure 1A:
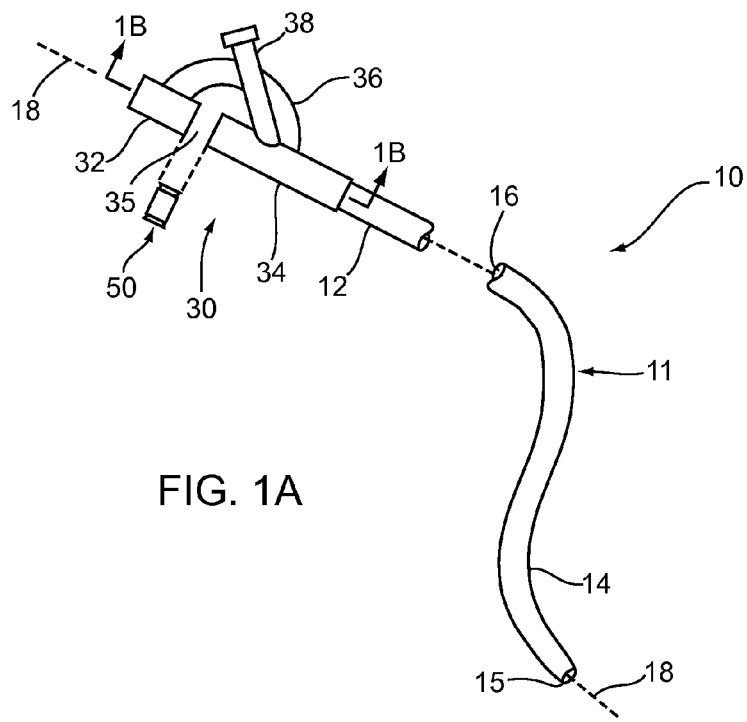
FIG. 1A is a perspective view of an exemplary embodiment of a tubular device, including a hub on its proximal end and a valve connectable to the hub.
Figure 1B:
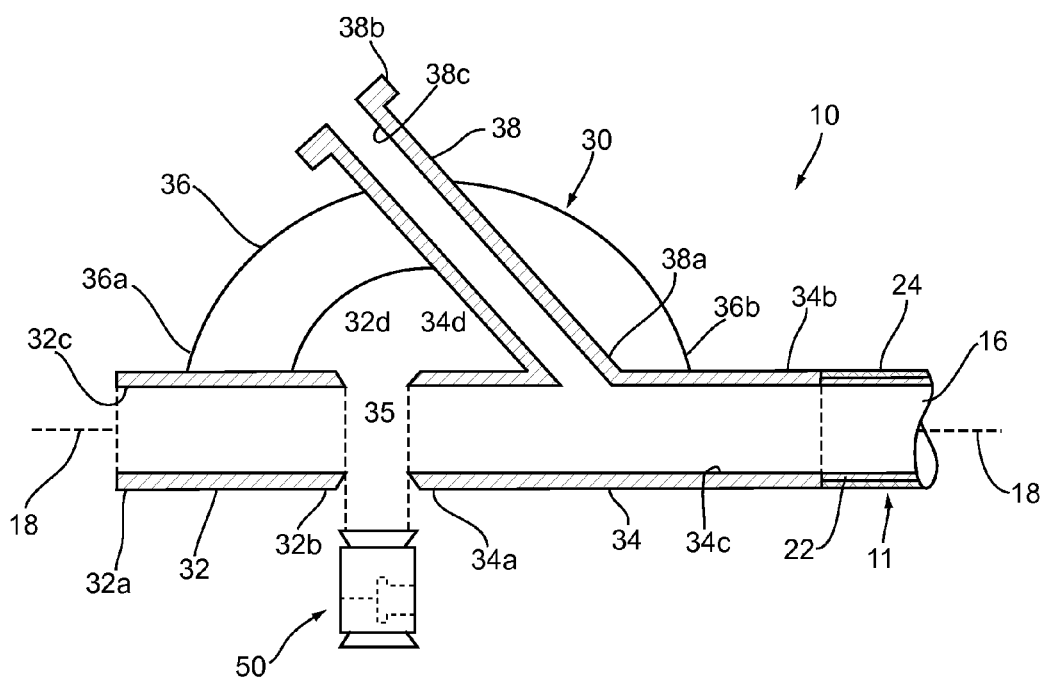
FIG. 1B is a cross-sectional view of the proximal end of the tubular device of FIG. 1A, taken along line 1B-1B, before the valve has been coupled to the hub.

Turning to the drawings, FIGS. 1A and 1B show an exemplary embodiment of an apparatus 10 for accessing a body lumen (not shown) and/or for delivering one or more fluids, agents, and/or instruments (also not shown) within a body lumen. In exemplary embodiments, the apparatus 10 may be a guide catheter, a procedure catheter, a sheath, an imaging device, or other tubular device sized for introduction into a body lumen, such as a vessel within a patient's vasculature, a passage within a patient's gastrointestinal tract, urogenital tract, reproductive tract, respiratory tract, lymphatic system, and the like.

Generally, the apparatus 10 includes an elongate tubular body 11 including a proximal end 12, a distal end 14 sized for introduction into a body lumen, a lumen 16 extending between the proximal and distal ends 12, 14 along a central longitudinal axis 18, and a handle or hub 30 on the proximal end 12 including a valve 50 for allowing one or more devices to be introduced and/or fluids to be infused into the lumen 16. Optionally, the apparatus 10 may include one or more additional lumens (not shown), which may be disposed concentrically around, side-by-side with, or otherwise adjacent the lumen 16. The lumen 16 may be sized for receiving a guide wire, procedure catheter, cardiac lead, needle, or other instrument (not shown), and/or for delivering fluids or other flowable agents or materials therethrough, as described further below.

As can be seen in FIG. 1B, the tubular body 11 may be constructed from one or more layers, e.g., an inner liner 22 surrounding the lumen 16, a reinforcing layer surrounding the inner liner (not shown), and an outer layer 24. Optionally, one or more coatings (not shown) may be applied to the inner surface of the inner liner 22. In an exemplary embodiment, a hydrophilic coating, such as Polyvinylpyrrolidone, may be sprayed or otherwise applied onto the surface of the inner liner 22 during fabrication to provide a lubricious inner surface for the lumen 16 of the tubular body 11. Exemplary materials and methods for making the tubular body 11 are disclosed in co-pending application Ser. No. 11/340,904, filed Jan. 26, 2006, Ser. No. 11/670,958, filed Feb. 2, 2007, Ser. No. 12/254,818, filed Oct. 20, 2008, and Ser. No. 12/551,540, filed Aug. 31, 2009. The entire disclosures of these references are expressly incorporated by reference herein.

The layers of the tubular body 11 may be attached to one another, e.g., by laminating, adhering, adhesive bonding, ultrasonic welding, reflowing or other heating, and the like. The construction of the tubular body 11 may be substantially uniform or may vary between the proximal and distal ends 12, 14, e.g., by varying the inner liner, 22, reinforcing layer, and/or outer layer 24 along the length of the tubular body 11. Optionally, the inner liner 22, reinforcing layer, and/or outer layer 24 may include one or more sublayers (not shown), which may vary in construction in various portions of the tubular body 11.

In one exemplary embodiment, the proximal end 12 may be substantially rigid or semi-rigid, e.g., providing sufficient column strength to allow the tubular body 11 to be pushed from the proximal end 12, while the distal end 14 may be substantially flexible or semi-rigid. Thus, the distal end 14 of the tubular body 11 may be advanced or otherwise manipulated within a patient's body from the hub 30 and/or proximal end 12 without substantial risk of buckling and/or kinking.

In exemplary embodiments, the tubular body 11 may have an outer diameter between about half and twenty millimeters (0.5-20 mm) or between about one and five millimeters (1-5 mm), and a length between about five and one hundred fifty centimeters (5-150 cm). The inner liner 22 may have a wall thickness between about 0.0001-0.01 inch (0.0025-0.25 mm) and the outer layer 24 may have a wall thickness between about 0.0005-0.2 inch (0.0127-5.08 mm).

The outer layer 22 may have a substantially homogenous construction between the proximal and distal ends 12, 14. Alternatively, the construction may vary along the length of the apparatus 10 to provide desired properties. For example, the outer layer 22a at or adjacent the proximal end 12 may be substantially rigid or semi-rigid, e.g., providing sufficient column strength to facilitate the apparatus 10 being pushed from the proximal end 12. In addition, the reinforcing layer or other material in the outer layer 22 may allow the apparatus 10 to be twisted from the proximal end 12, e.g., to rotate the distal end 14 within a patient's body. Thus, the distal end 14 of the apparatus 10 may be manipulated within a patient's body from the proximal end 12 without substantial risk of buckling and/or kinking. Optionally, the outer layer 22b at or adjacent the distal end 14 may be substantially flexible or semi-rigid, e.g., to allow the distal end 14 to bend easily or otherwise be advanced through tortuous anatomy and/or provide a substantially atraumatic distal tip 15. Furthermore, the outer layer 22a, may have one or more transition regions along its length, transitioning from one desired construction to another. Exemplary outer layers that may be included in the apparatus 10 and methods for making them are disclosed in U.S. Pat. Nos. 4,478,898, 4,863,442, 5,217,440, 5,254,107, 5,676,659, 5,811,043, 5,836,926, 6,004,310, 6,669,886, 6,837,890, and 6,945,970. The entire disclosures of these references are expressly incorporated by reference herein.

Optionally, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, needles, and the like (not shown), depending upon the particular intended application for the apparatus 10.

Returning to FIG. 1B, an exemplary embodiment of a hub 30 (which may be any of the embodiments described herein) is shown that includes a first or proximal hub portion 32 and a second or distal hub portion 34 coupled together by a hub arm 36. The first hub portion 32 may be an elongate tubular body including a first end 32a, a second end 32b, and a first hub lumen 32c extending therebetween. Similarly, the second hub portion 34 may be an elongate tubular body including a first end 34a, a second end 34b, and a second hub lumen 34c extending therebetween. The lengths of the first and second hub portions 32, 34 may substantially the same or different than one another, e.g., between about 0.1 and ten centimeters (0.1-10 cm).

The hub portions 32, 34 may have a substantially uniform wall thickness. Alternatively, the thickness of the hub portions 32, 34 may vary around a circumference of the hub portions 32, 34. For example, the hub portions 32, 34 may include a relatively thin or weakened region (not shown) extending axially along the hub portions 32, 34, e.g., to facilitate slitting the hub 30 during use, as explained further below. In an exemplary embodiment, the relatively thin region may be disposed generally opposite the hub arm 36, e.g., such that the relatively thin region may be slit or cut without substantial interference from the hub arm 36.

The first and second hub portions 32, 34 may be aligned with one another such that the first and second hub lumens 32c, 34c are also aligned with one another, e.g., concentrically around the longitudinal axis 18 of the apparatus 10. The hub lumens 32c, 34c may be sized to accommodate slidably receiving a medical device therethrough, e.g., having a diameter between about one and ten millimeters (1-10 mm), which may allow introduction of a medical device through the hub 30 into the tubular body 11, as explained further below. Alternatively, the hub portions 32, 34 and/or hub lumens 32c, 34c may have an elliptical or other cross-section rather than a circular cross-section, if desired.

The first end 32a of the first hub portion 32 may include a transition and/or other features to facilitate introducing a medical device into the first hub lumen 32c. For example, the first end 32a may include a tapered wall (not shown) communicating with the first hub lumen 32c. The second end 34b of the second hub portion 34 may include one or more connectors (not shown) for attaching the tubular body 11 to the hub 30. For example, the second end 34b may include one or more tabs, slots, threads, and the like (not shown) that may be engaged with complementary slots, tabs, threads, and the like (also not shown) on the proximal end 12 of the tubular body 11. In addition or alternatively, the second end 34b may be engaged with the proximal end 12 by an interference fit, may be attached by bonding with adhesive, fusing, sonic welding, heat bonding, reflowing, insert molding, and the like, if desired.

As shown in FIG. 1B, the arm 36 may include a first end 36a attached to the first hub portion 32 and a second end 36b attached to the second hub portion 34, thereby maintaining the first and second hub portions 32, 34 spaced apart from one another to define a gap 35. In an exemplary embodiment, the hub portions 32, 34 may be spaced apart such that the gap 35 has an axial length (substantially parallel to the longitudinal axis 18) or other size, e.g., between about one and ten millimeters (1-10 mm). The arm 36 may be sufficiently flexible such that the first hub portion 32 may be directed away from the second hub portion 34 to increase an axial length or other size of the gap 35, e.g., to accommodate inserting the valve 50 within the gap 35, as explained further below.

For example, during manufacturing or otherwise before use, the hub portions 32, 34 may be directed slightly apart from one another to increase the length of the gap 35 while a valve 50 is inserted within the gap 35. When the hub portions 32, 34 are released, the hub portions 32, 34 may return to their original position, e.g., engaging or otherwise capturing the valve 50 within the gap 35, as explained further below. As shown in FIG. 1B, the arm 36 may have an arcuate shape, e.g., a curved shape having a substantially uniform or varying radius of curvature between the first and second ends 36a, 36b. The shape and/or material of the arm 36 may accommodate bending the arm 36 open slightly when the hub portions 32, 34 are directed apart, and automatically returning the arm 36 to its original shape when the hub portions 32, 34 are released, thereby returning the hub portions 32, 34 to their original relative positions. Alternatively, the arm 36 may have other shapes, which may be flexible to accommodate inserting the valve 50 within the gap 35.

Figure 8A:
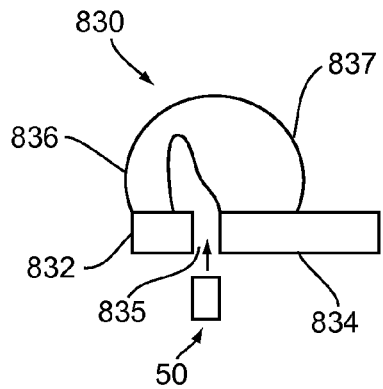
FIGS. 8A-8C are side views of yet another embodiment of a handle showing a method for securing a valve to the handle.
Figure 8B:
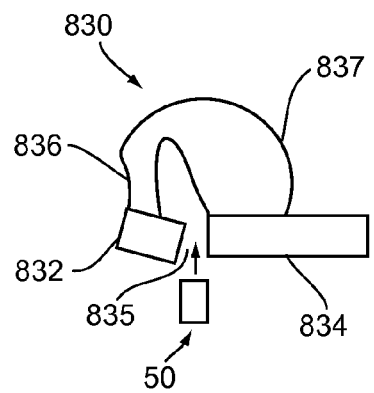
Figure 8C:
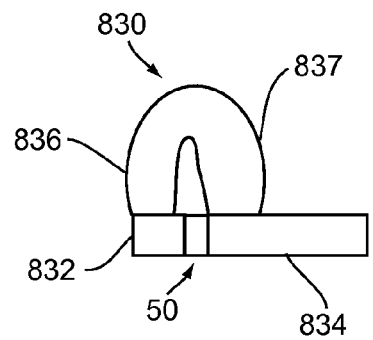

For example, turning to FIGS. 8A-8C, another embodiment of a hub 830 is shown that includes a proximal or first handle portion 836 coupled to a distal or second handle portion 847. The first handle portion 836 may include a first hub portion 832 and the second handle portion 837 may include a second hub portion 834 that are spaced apart when the hub 830 is free from external forces to define a gap 835, as shown in FIG. 8A. The first handle portion 836 may be sufficiently flexible that the first handle portion 836 may be bent to direct the first hub portion 832 away from the second hub portion 834 and open the gap 835. For example, as shown in FIG. 8B, the first handle portion 836 may be relatively narrower in cross-section than the second handle portion 837 to provide sufficient flexibility to resiliently bend the first handle portion 836. Once a valve 50 is inserted into the expanded gap 835 and/or attached to one of the hub portions 832, 834, the first handle portion 836 may be released and/or otherwise allowed to resiliently return to its original position, thereby capturing the valve 50 between the hub portions 832, 834, as shown in FIG. 8C.

Figure 9A:
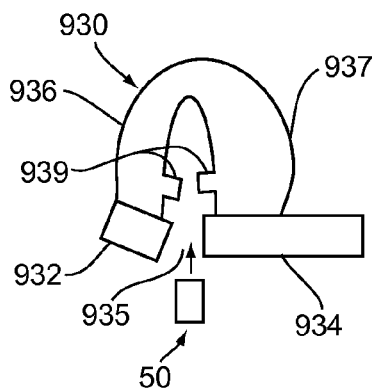
FIGS. 9A and 9B are side views of still another embodiment of a handle showing a method for securing a valve to the handle.
Figure 9B:
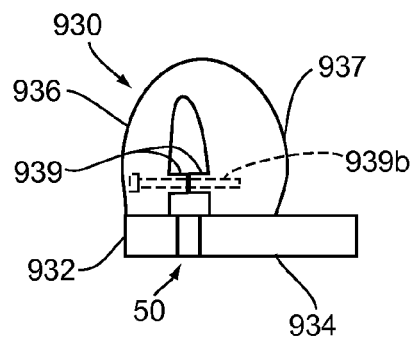

Turning to FIGS. 9A and 9B, an alternative embodiment of a hub 930 is shown that includes first and second handle portions 936, 937 with respective hub portions 932, 934. In this alternative, the handle portions 936, 937 may be substantially rigid but may be pivotally coupled together, e.g., opposite the hub portions 932, 934, such that the handle portions 936, 937 may be opened or closed to increase or decrease a gap 935 between the hub portions 936, 937. Unlike the previous embodiments, the handle portions 936, 937 include opposing stops or other features 939a that are configured to limit movement of the handle portions 936, 937 to an orientation providing the desired gap 935.

For example, as shown in FIG. 9A, the hub 930 may be provided initially with the stops 939a spaced apart from one another such that the gap 935 is larger than the size for the selected valve 50. Once the vale 50 is positioned within the gap 935 and/or attached to one of the hub portions 932, 934, the first handle portion 936 may be pivoted towards the second handle portion 937 until the stops 939a abut or otherwise contact one another to capture the valve 50 in the final gap 935. The handle portions 936, 937 may be plastically deformed when pivoted to close the gap 935, e.g., such that the handle portions 936, 937 remain in the final orientation shown in FIG. 9B. In addition or alternatively, one or more fasteners 939b may be coupled between the handle portions 936, 937, e.g., through the stops 939a, as shown. In addition or alternatively, the stops 939a may be attached together by bonding with adhesive, fusing, sonic welding, cooperating detents or other connectors, and the like (not shown). Optionally, the valve 50 may also be attached to one or both hub portions 932, 934, e.g., similar to other embodiments herein.

Figure 10A:
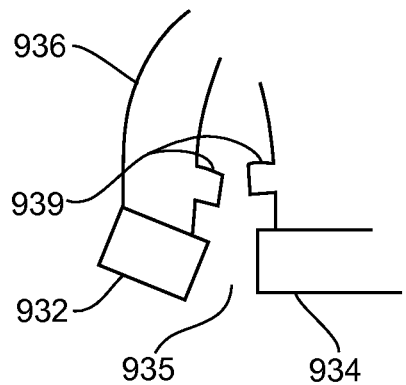
FIGS. 10A and 10B are details of the handle of FIGS. 9A and 9B.
Figure 10B:
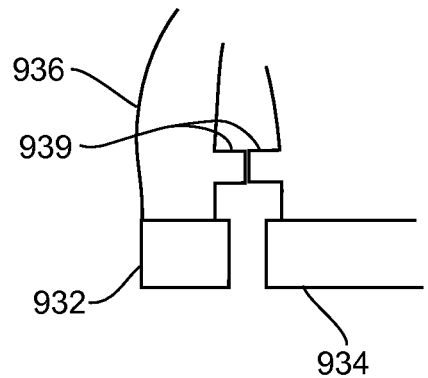

Turning to FIGS. 10A and 10B, the opposing surfaces of the hub portions 932, 934 defining the gap 935 may not be substantially parallel to one another when the gap 935 is opened, as shown in FIG. 10A. The angle of the opposing surfaces may correspond generally to the degree that the first handle portion 936 is rotated when the gap 935 is closed, e.g., such that the opposing surfaces are substantially parallel to one another or are otherwise configured to capture the valve 50 when the stops 939 engage one another, as shown in FIG. 10B.

Figure 11:
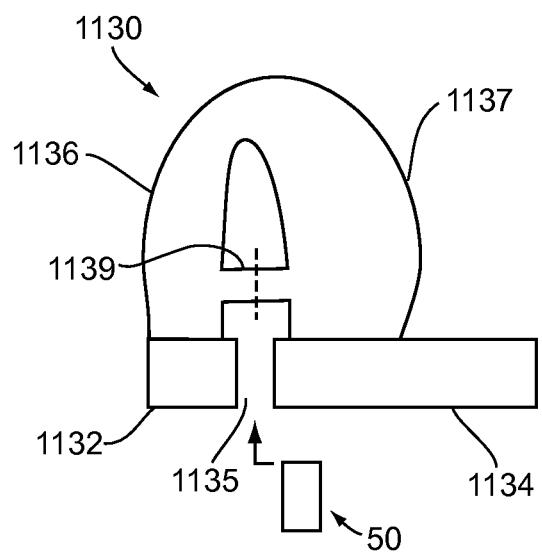
FIG. 11 is a side view of yet another embodiment of a handle for receiving a valve.

Turning to FIG. 11, yet another embodiment of a hub 1130 is shown that includes first and second handle portions 1136, 1137 pivotally coupled to one another, e.g., generally opposite a gap 1135 between hub portions 1132, 1134 on respective handle portions 1136, 1137. The hub 1130 also includes a bridge feature 1139 extending between the handle portions 1136, 1137, e.g., adjacent the gap 1135. For example, the hub 1130 may be molded or otherwise integrally formed as a single piece including the handle portions 1136, 1137, hub portions 1132, 1134, and bridge 1139.

To accommodate capturing a valve 50, the bridge 1139 may be cut or otherwise severed to create stops, thereby allowing the handle portions 1136, 1137 to pivot away from one another (similar to FIG. 9A) to increase the size of the gap 1135. With the gap 1135 opened, the valve 50 may be positioned in the gap 1135 and/or attached to one of the hub portions 1132, 1134. The handle portions 1136, 1137 may then be released or otherwise returned to their original orientation. For example, the pivot point of the handle portions 1136, 1137 may be biased to return towards its original configuration or the handle portions 1136, 1137 may be plastically deformed to close the gap 1135 and capture the valve 50, e.g., when the stops 1139 contact one another. In addition, if desired, one or more fasteners 1139b may be directed through the stops 1139 or otherwise between the first and second handle portions 1136, 1137 to secure the hub 1130 with the valve 50 captured between the hub portions 1132, 1134. In addition or alternatively, the stops 1139 and/or the first and second handle portions 1136, 1137 may be attached together by bonding with adhesive, fusing, sonic welding, cooperating detents or other connectors, and the like (not shown). Optionally, the valve 50 may also be secured to the hub portions 1132, 1134, e.g., by bonding with adhesive, fusing, sonic welding, and the like in addition or instead of the fastener(s).

In a further alternative, with general reference to FIG. 1B, the arm 36 and/or hub 30 may be substantially rigid and/or the gap 35 substantially fixed. In this alternative, the hub or handle may be formed as separate components that are attached together when a valve is being secured to the handle, as described further below.

In addition or in a further alternative, e.g., where the hub 30 is substantially rigid, the valve 50 may be inserted into the gap 35 by temporarily deforming the valve 50. The valve 50 may then return to its original shape, thereafter being engaged within the gap 35. The valve 50 may be introduced into the gap 35 from the side or through the hub lumen 32c or 34c of the hub portion 32 or 34. Optionally, if desired, the arm 36 may have other shapes adapted to enable secure gripping of the arm 36 for manipulation of the apparatus 10, including, for example, advancing, retracting or rotating within a body lumen, and/or removal of the apparatus 10 by slitting.

Optionally, the second end 32b of the first hub portion 32 and/or the first end 34a of the second hub portion 34 may include one or more connectors (not shown) for cooperating with complementary connectors on the valve 50 and/or for otherwise engaging the valve 50 captured within the gap 35. For example, the ends 32b and/or 34a may include one or more tabs, slots, threads, features and the like (not shown), which may be engaged with complementary slots, tabs, threads, features and the like (also not shown) on the valve 50. Alternatively, or in addition, as shown in FIG. 1B, the ends 32b, 34a may include beveled edges 32d, 34d extending around a circumference of the ends 32b, 34a that may be captured in corresponding slots 58 in the valve 50, as explained further below.

Returning to FIG. 1B, the hub 30 (or any of the other hubs or handles described herein) may also include one or more side ports, e.g., a first side port 38 communicating with the lumen 16. Optionally, one or more additional side ports (not shown) may be provided on the hub 30 communicating with respective lumen(s), e.g., if the tubular body 11 includes an inflation lumen for a balloon on the distal end 14 (also not shown). The side port 38 generally includes a tubular body including a first end 38a coupled to the second hub portion 34, a second end 38b including a connector (not shown), and a lumen 38c extending from the second end 38b to the first end 38a and communicating with the second hub lumen 34c. In an exemplary embodiment, the connector on the second end 38b may include a luer lock connector, a hemostatic seal, and the like, e.g., for coupling a source of fluid, inflation media, and/or vacuum to the side port 38.

Optionally, the hub 30 may include one or more other connectors, e.g., luer lock connectors, electrical connectors, and the like (not shown), for connecting other devices (not shown) to the apparatus 10, such as syringes, displays, controllers, and the like (also not shown). In addition, the hub 30 may include one or more actuators, such as sliders, buttons, switches, and the like, e.g., for activating and/or manipulating components (also not shown) on the distal end 14 or otherwise operating the apparatus 10.

Multiple components of the hub 30 may be integrally formed together as a single piece or may be formed separately and then attached together to provide the hub 30. For example, the hub portions 32, 34, arm 36, and side port 38 may be formed as a single piece, e.g., by injection molding, casting, and the like. Alternatively, as described further elsewhere herein, the hub portions 32, 34 and side port 38 may be formed separately, e.g., by extrusion, injection molding, casting, and the like, and attached to the hub arm 36 and/or to each other, as desired, e.g., using cooperating connectors (not shown), bonding with adhesive, fusing, sonic welding, heat bonding, reflowing, insert molding, and the like. The hub 30 and/or its components may be formed from plastic, metal, or composite materials, as desired, such as nylon, PEBAX, PTFE, HDPE, and the like.

Figure 12A:
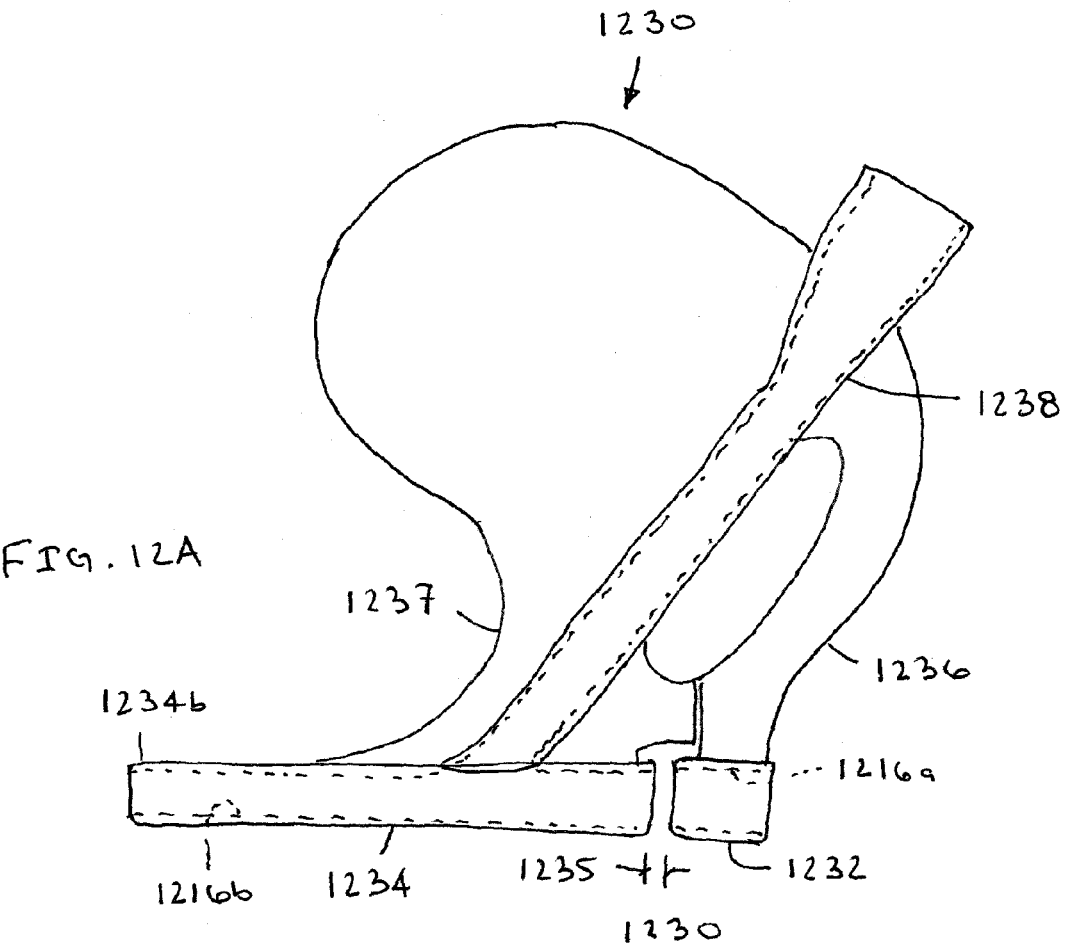
FIG. 12A is a side view of still another embodiment of a hub for a tubular medical device, such as that shown in FIGS. 1A and 1B.
Figure 12B:
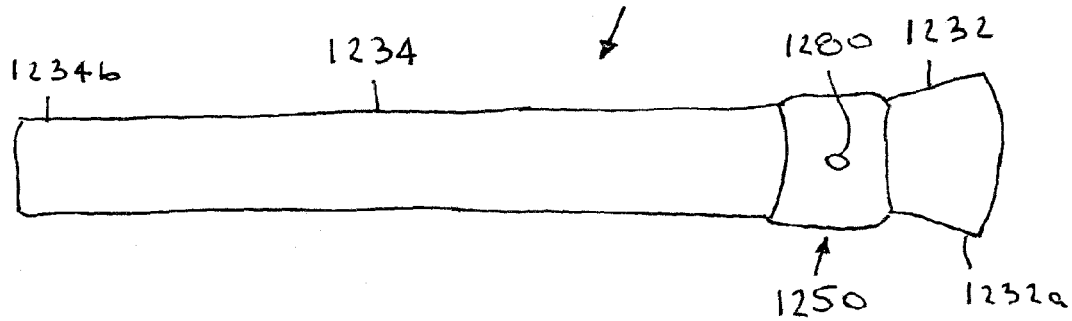
FIG. 12B is a bottom view of the hub of FIG. 12A including a valve coupled to the hub.

Turning to FIGS. 12A and 12B, another embodiment of a hub 1230 is shown that includes a proximal or first handle portion 1236 coupled to a distal or second handle portion 1237. The first handle portion 1236 may include a first hub portion 1232 and the second handle portion 1237 may include a second hub portion 1234 that are spaced apart when the hub 1230 is free from external forces to define a gap 1235, as shown in FIG. 12A. The second handle portion 1237 may include a side port 1238 communicating with a lumen 1216*b* of the second hub portion 1234, similar to other embodiments herein. The hub 1230 may be fabricated using methods and materials similar to any of the other embodiments herein.

Similar to other embodiments, the first handle portion 1236 may be sufficiently flexible that the first handle portion 1236 may be bent or pulled away from the second handle portion 1237 to direct the first hub portion 1232 away from the second hub portion 1234 and open the gap 1235, similar to other embodiments herein. For example, the first handle portion 1236 may be relatively narrower in cross-section than the second handle portion 1237 to provide sufficient flexibility to resiliently bend the first handle portion 1236. Once a valve 1250 (which may be any of the embodiments herein) is inserted into the expanded gap 1235 and/or attached to one of the hub portions 1232, 1234, the first handle portion 1236 may be released and/or otherwise allowed to resiliently return to its original position, thereby capturing the valve 1250 between the hub portions 1232, 1234, as shown in FIG. 12B.

A first end 1232*a* of the first hub portion 1232 may include a transition and/or other features to facilitate introducing a medical device into a first hub lumen 1216*a* of the first hub portion 1232. For example, the first end 1232*a* may include a tapered wall communicating with the first hub lumen 1216*a* to provide an inlet having a diameter or other cross-section larger than the second end portion 1234. In addition or alternatively, the first end 1232*a* may include a connector or fitting, including, for example, a luer connector (not shown). Optionally, a distal or second end 1234*b* of the second hub portion 34 may include one or more connectors (not shown) for attaching a tubular body (also not shown) to the hub 1250, also similar to other embodiments herein.

Turning to FIGS. 2A-2C, an exemplary embodiment of a serial valve 50 is shown that generally includes a valve body 52 including a proximal or first end 54, a distal or second end 56, an outer surface 57 extending between the first and second ends 54, 56, and a valve passage 60 extending between the first and second ends 54, 56. As shown, the valve passage 60 includes a bore 62 and a slit 64 that are formed adjacent one another within the valve body 52. For example, the bore 62 may extend from the first end 54 partially through the valve body 52 to an intermediate region such that the bore 62 defines a bottom surface 68, and the slit 64 may extend from the bore 62, e.g., from the bottom surface 68, to the second end 56 of the valve body 52. As explained further below, the bore 62 may allow the valve 50 to provide a substantially fluid-tight seal when a medical device (not shown) is inserted into the valve passage 60, while the slit 64 may provide a fluid-tight seal when the valve passage 60 is empty (i.e., without a medical device inserted into the valve passage 60).

Optionally, the valve passage 60 may also include a recess 69, e.g., at the bottom 68 of the bore 62. For example, the recess 69 may extend circumferentially around the bore 62 adjacent the bottom 68 to define an annular pocket within the valve passage 60 that has a diameter or other cross-section that is larger than the bore 62. For example, with the valve body 52 in a relaxed state (e.g., without a medical device, tool, or other instrument inserted into the bore 62), the bore 62 may have a diameter between about 0.25 and eight millimeters (0.25-8 mm), and the recess 69 may a diameter larger than the bore 62 between about 0.3 and nine millimeters (0.3-9 mm). Alternatively, one or more discrete recesses or pockets (not shown) may be provided within the bore 62, e.g., spaced apart from one another circumferentially around the bore 62 and/or axially along the bore 62, if desired. Such recess(es) may accommodate providing a lubricant within the valve passage 60, e.g., to reduce friction or otherwise facilitate introducing a medical device, tool, or other instrument into the valve passage 60, as explained further below. In addition or alternatively, the recess 69 may facilitate expansion of the bore 62, e.g., when a medical device, tool, or other instrument is inserted into the bore 62, also as explained further below. In addition or alternatively, the recess 69 may be adapted decrease or stop propagation of tears during expansion of the bore 62 or slit 64, e.g., when a medical device, tool, or other instrument is inserted through the valve body 52, as described further below.

As best seen in FIGS. 2B and 2C, the valve body 52 may be formed such that both the outer surface 57 and bore 62 extend substantially parallel to the longitudinal axis 18. However, as best seen in FIGS. 2A and 2B, a central axis 66 of the bore 62 may be offset from the longitudinal axis 18, e.g., such that the bore 62 is closer to the outer surface 57 of the valve body 52 on one side than the opposite side. Thus, a side wall region of the valve body 52 adjacent the bore 62 may be thinner on one side of the valve body 52 than other side wall regions, which may facilitate slitting the valve 50 during use, as explained further below.

The bore 62 may be sized appropriately to allow a medical device (not shown) to pass freely through the bore 62 without substantial frictional resistance and/or to provide a seal around the medical device to prevent substantial fluid leakage when the medical device is passed through the bore 62. Optionally, the valve body 52 may be resiliently flexible such that the bore 62 may be dilated or otherwise expanded when a medical device is inserted into the bore 62 and may resiliently return to its original size when the medical device is removed. Thus, the bore 62 may expand to accommodate a medical device having a larger cross-section than the bore 62 with the valve body 52 in the relaxed state. For example, with the valve body 52 in the relaxed state (e.g., without a medical device inserted into the bore 62), the bore 62 may have a diameter between about 0.25 and eight millimeters (0.25-8 mm), but may be expandable to larger diameters, e.g., between about 0.35 and ten millimeters (0.35-10 mm).

The slit 64 may also extend substantially parallel to the longitudinal axis 18 from the bottom 68 of the bore 62 to the second end 56 of the valve body 52, as best seen in FIG. 2C. Alternatively, two or more intersecting slits (not shown) may extend from the bottom 68 of the bore 62 to the second end 56 of the valve body 52, for example in an intersecting cross pattern (not shown). As best seen in FIG. 2A, the slit 64 may have a width at least as long as the diameter of the bore 62, and, optionally, may have a length greater than the diameter of the bore 62, e.g., between about 0.25 and eight millimeters (0.25-8 mm). The width of the slit 64 may be substantially uniform between the bottom 68 of the bore 62 and the second end 56 of the valve body 52 or may vary along its length. For example, the width of the slit 64 may be greater adjacent the bore 62 than at the second end 56 of the valve body 52, if desired.

The width of the slit 64 may be sufficient to allow opposing regions of the valve body 52 on either side of the slit 64 to be directed away from one another to accommodate receiving a medical device through the valve passage without substantial risk of the valve body 52 tearing uncontrollably. Thus, the valve body 52 may be resiliently flexible such that the opposing slit regions may expand when a medical device is inserted through the slit 64, yet resiliently close when the medical device is removed to maintain a substantially fluid tight seal through the valve passage 60. Alternatively, the slit 64 may provide a relatively small passage to guide a medical device from the bore 62 through the valve body 52 to the second end 56, e.g., with the slit 64 providing a preferential tear line through the valve body 52 as the medical device is inserted therethrough. In another alternative, the valve body 52 may include features, such as the recess 69, which may decrease or stop propagation of tears initiated as a medical device is inserted therethrough.

Optionally, the valve body 52 may include one or more additional features. For example, as shown in FIG. 2D, an alternative valve body 52' is shown that includes a first end 54' that is at least partially tapered, e.g., to facilitate introduction of a medical device therethrough and/or into the bore 62.' As shown, the first end 54' includes a surface 55' that tapers from the first end 54' into the bore 62,' which may guide a medical device introduced into a hub (not shown) towards the bore 62.' For example, if the medical device has a diameter smaller than the first hub lumen 32c (not shown, see, e.g., FIG. 3), the tapered surface 55' may facilitate guiding the medical device inserted into the first hub lumen 32c through the valve 50' and into the second hub lumen 34c.

In addition or alternatively, the valve body 52' may include a convex or otherwise shaped second end 56' that includes less material towards the outer surface 57' of the valve body 52' than towards the central longitudinal axis 18.' Such a shape may facilitate directing opposing slit regions away from one another when a medical device is inserted into the slit 64' since there is less material to bunch up adjacent the wall of the second hub portion 34 (not shown, see, e.g., FIG. 3). Such a shape may also distribute forces within the valve body 52' when a medical device is inserted into the slit 64' to prevent undesired tearing of the valve body 52.' Such a shape may also facilitate sealing the valve when no medical device is inserted into the slit 64' and pressure is applied to the second end 56.'

Returning to FIGS. 2A-2C, the valve body 52 may be formed from an elastomeric material, such as silicone, chronoprene, isoprene, santoprene, and the like. In one embodiment, the valve body 52 may be integrally formed as a single piece, e.g., by injection molding, casting, and the like. For example, with continued reference to FIG. 2A, the valve body 52, including connectors 58, bore 62, and recess 69, may be integrally formed, e.g., by injection molding, casting, and the like. Alternatively, the valve body 52 may be formed as a solid body and the connectors 58, bore 62, and/or recess 69 may be formed into the solid body, e.g., by cutting, machining, and the like.

Figure 4A:
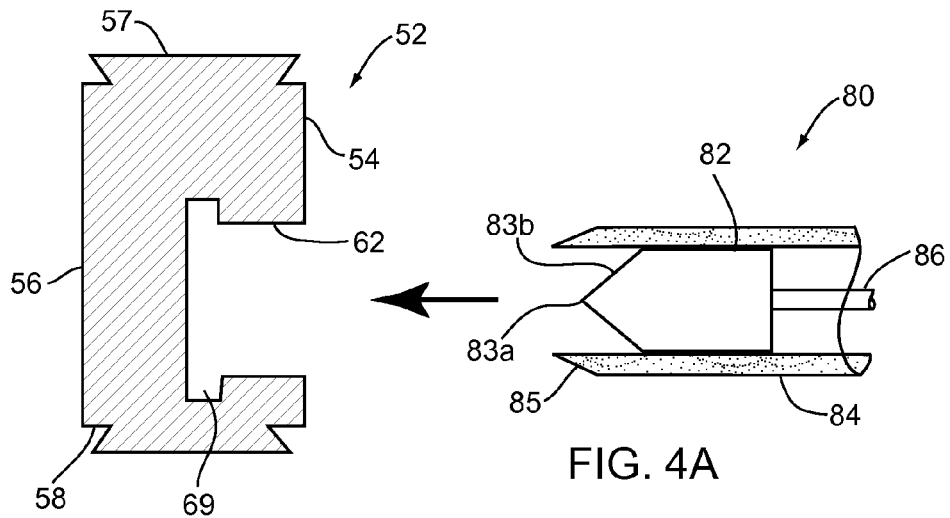
FIGS. 4A-4C are cross-sectional views of a valve body showing a method for making a slit through the valve body to create the valve of FIGS. 2A-2C.
Figure 4B:
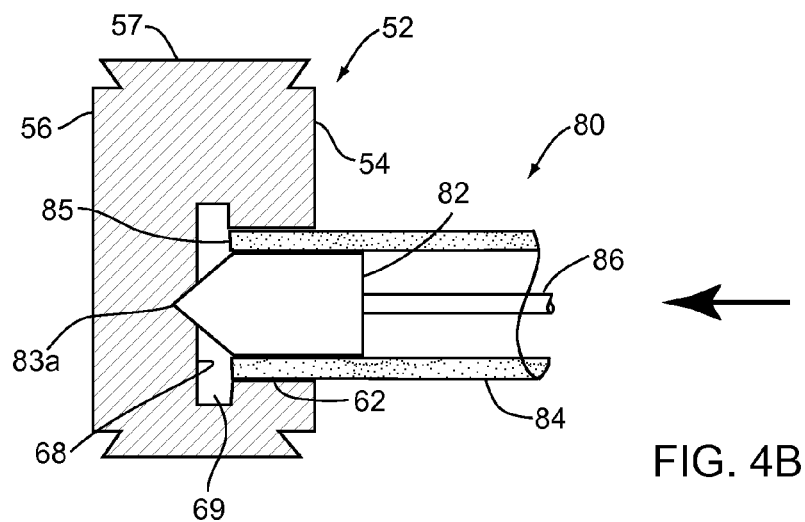
Figure 4C:
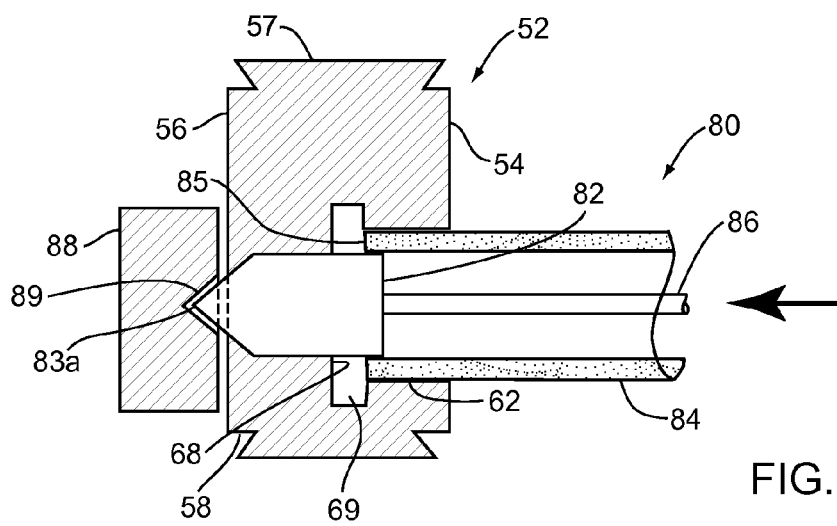

Once the valve body 52 including the bore 62 are formed, the slit 64 may be formed in the valve body 52, e.g., to complete the valve passage 60. Turning to FIGS. 4A-4C, an exemplary method is shown for forming the slit 64 in the valve body 52 of FIGS. 2A-2C. Initially, as shown, a valve body 52 may be provided including a bore 62 (and optionally recess 69) formed therein, as described above. A tool 80 may be provided to cut or otherwise penetrate through the valve body 52 to create the slit 64. For example, the tool 80 may include a blade or other cutting element 82 for mechanically cutting or slicing through the valve body 52, although alternatively other devices may be used, for example, a heated blade, wire, or other element that may melt through the valve body 52, e.g., in addition to or instead of mechanically cutting the valve body 52.

As shown in FIGS. 4A-4C, the tool 82 includes a blade or other mechanical cutting element 82, e.g., having a width corresponding the desired width of the slit 64 to be formed. In addition or alternatively, the cutting element 82 may have a relatively thin thickness, e.g., between about 0.05 and 0.75 millimeter (0.05-0.75 mm), to facilitate advancing the cutting element 82 through the material of the valve body 52 with minimal friction and/or risk of tearing the valve body 52. As shown, the cutting element 82 may include a sharpened tip 83a and/or one or more sharpened edges 83b (two shown), which may facilitate cutting into the material of the valve body 52.

Optionally, the cutting element 82 may be deployable from a sleeve or other assembly 84, e.g., such that the cutting element 82 may be initially provided within the sleeve 84 and may be advanced from and/or retracted into the sleeve 84 when desired. For example, the tool 80 may include a handle (not shown) coupled to a proximal end of the sleeve 84 that includes an actuator (also not shown) coupled to a shaft or other actuator member 86 carrying the cutting element 82.

Optionally, as shown in FIG. 4C, the tool 80 may include a rigid stop 88, which may be placed opposite the sleeve 84 and cutting element 82 to facilitate penetrating the cutting element 82 sufficiently into the valve body 52. For example, the stop 88 may include a slot or other recess 89 that may be sized to receive at least the tip 83a of the cutting element 82 therein, e.g., to ensure that the cutting element 82 penetrates a sufficient depth into or through the valve body, as described further below.

The sleeve 84 may include a distal end 85 which may be tapered, as shown in FIG. 4A, e.g., to provide a transition that facilitates advancing the sleeve 84 at least partially into the bore 62 of the valve body 52. Alternatively, the distal end 85 may be blunt, e.g., as shown in FIGS. 4B and 4C, or otherwise shaped. The distal end 85 of the sleeve 84 may have a diameter or other cross-section smaller than the bore 62 in its relaxed state, e.g., such that the distal end 85 may be inserted into the bore 62 without deforming the valve body 52, e.g., before deploying the cutting element 82. Alternatively, the distal end 85 of the sleeve 84 may be larger than the bore 62, e.g., such that the bore 62 may be expanded when the sleeve 84 is inserted therein, as shown in FIGS. 4B and 4C. In this alternative, the cutting element 82 may have a width greater than the diameter of the bore 62 in the relaxed state, e.g., to form a slit 64 having a width greater than the diameter of the bore 62.

Turning to FIG. 4A, the cutting element 82 is shown retracted within the sleeve 84 and the sleeve 84 is directed towards the valve body 50, i.e., into the bore 62. As shown in FIG. 4B, the distal end 85 of the sleeve 84 has been inserted into the bore 62, e.g., until the distal end 85 contacts or is immediately adjacent the bottom 68 of the bore 62. As shown, the bore 62 has been expanded by the distal end 85 of the sleeve 84 to a diameter approaching the diameter of the recess 69, although alternatively, the bore 62 may be expanded further, which may also expand the recess 69.

Turning to FIG. 4C, the cutting element 82 has been advanced from the sleeve 84 such that the distal tip 83a penetrates through the bottom 68 of the bore 62 and through the valve body 52 and at least partially out through the second end 56. Thus, the cutting element 82 has created a slit 64 that extends from the bottom 68 of the bore 62 through to the second end 56 of the valve body 52. As shown, the distal tip 83a of the cutting element 82 has exited the valve body 52 and entered the slot 89 in the stop 88. The stop 88 may also prevent deformation of the valve body 52 when the cutting element 82 is advanced through the second end 56, thereby reducing the risk of tearing or otherwise damaging the valve body 52.

The cutting element 82 may be retracted back into the sleeve 84 and the sleeve 84 removed from the bore 62, thereby providing a slit 64 extending through the valve body 52, as shown in FIGS. 2A-2C. In an alternative embodiment, the cutting element 82 or other tool may be used to create the slit 64 by penetrating the second end 56 of the valve body 52, e.g., through the bottom 68 of the bore 62, if desired, rather than through the bore 62 from the first end 54 of the valve body 52.

Optionally, lubricant or other material may be introduced into the bore 62, e.g., into the recess 69. Any additional features may be formed in the valve body 52, if desired, to create the final valve 50. The valve 50 may thereafter be incorporated into a hub or other apparatus.

Turning to FIGS. 13A-13E, another exemplary embodiment of a serial valve 1250 is shown that generally includes a valve body 1252 defining a central longitudinal axis 1218, a valve support 1270 extending radially outwardly from the valve body 1252, and flanged connectors 1272 extending from the valve support 1270, e.g., substantially parallel to the central axis 1218, for coupling the valve 1250 to a hub (not shown), as described further below. Generally, the valve body 1252 includes a first, proximal, or inlet end 1254 and a second, distal, or outlet end 1256, e.g., each defining substantially planar surfaces extending substantially perpendicular to the central axis 1218. The valve body 1252 also includes a bore 1260 extending from the inlet end 1254 partially through the valve body 1252, and a cover 1282 adjacent the outlet end 1256 for resiliently sealing the bore 1260, as described further below. The valve body 1252 also includes a generally circular or other peripheral outer surface 1262 extending from the outlet end 1256 at least partially towards the inlet end 1254, e.g., such that the outer surface 1262 extends substantially parallel to and around the central axis 1218, that at least partially defines the cover 1282, as described further below.

Figure 13C:
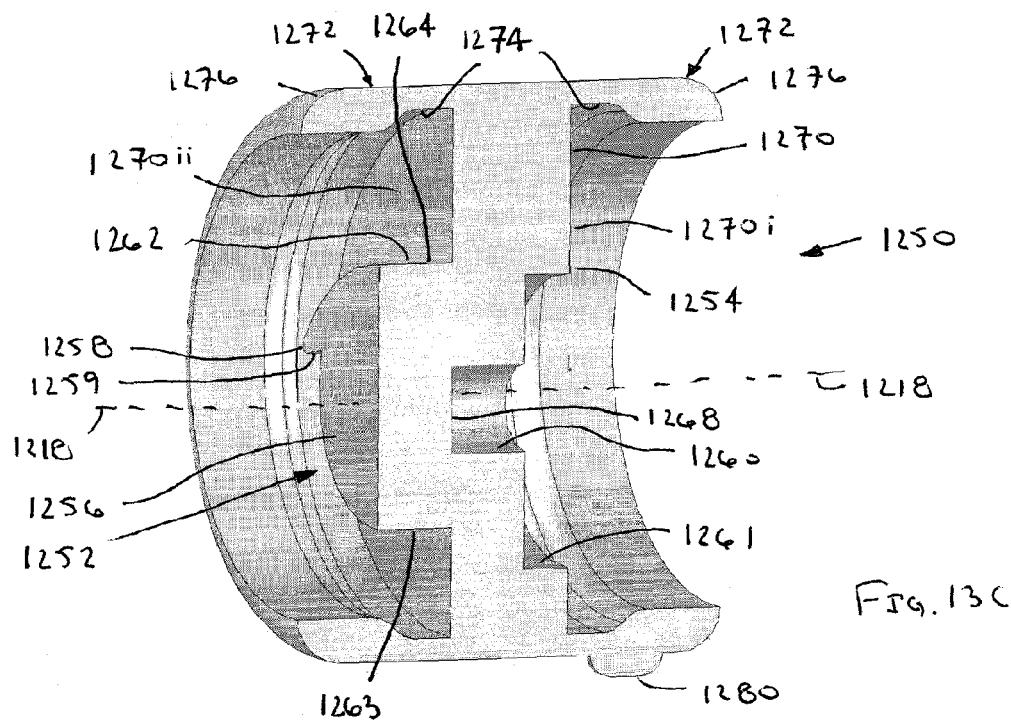
FIG. 13C is a cut-away perspective view of the valve of FIGS. 13A and 13B, taken along line 13C-13C.
Figure 13D:
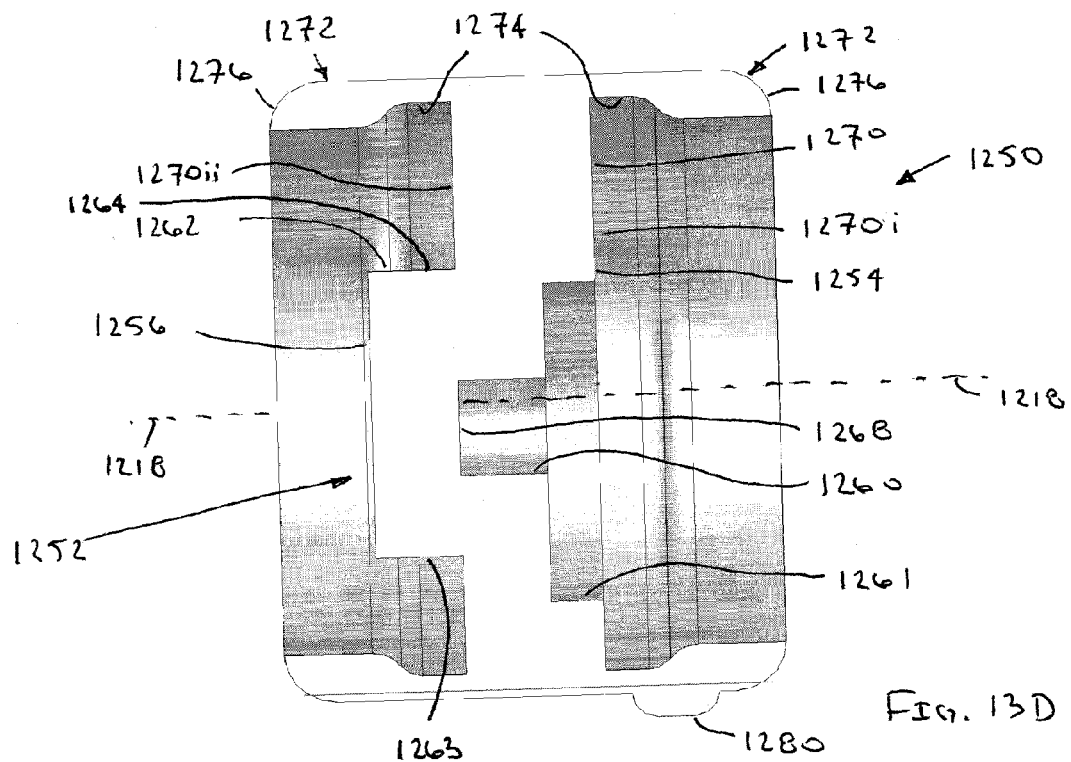
FIG. 13D is a cross-sectional view of the valve of FIGS. 13A and 13B, taken along line 13C-13C.
Figure 17A:
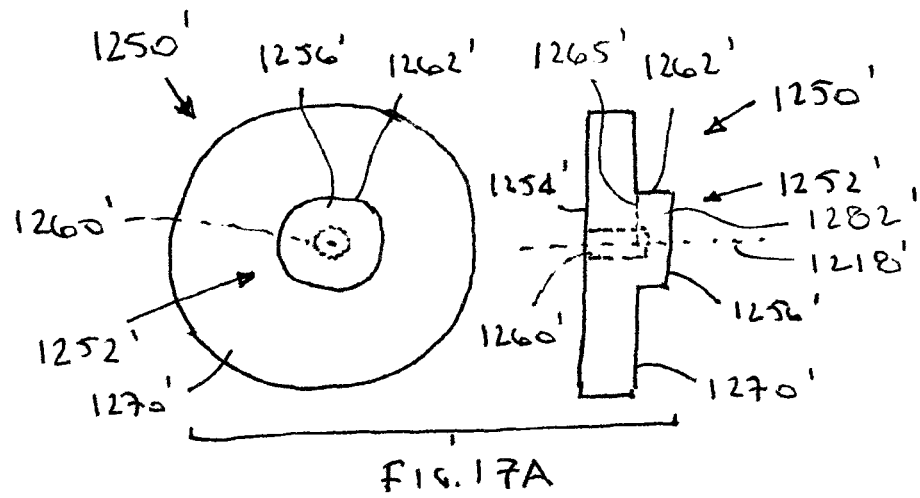
FIGS. 17A-17C are end and side views of alternative embodiments of valve bodies that may be incorporated into a valve, such as the valve of FIGS. 13A and 13B.

As best seen in FIGS. 13B and 13E, the outer surface 1262 of the valve body 1252 has a generally circular shape, which may be disposed around the central axis 1218. As shown, the valve body 1252 may be offset laterally from the central axis 1218, e.g., such that a first or lower side 1263 of the outer surface 1262 is disposed closer to the flanged connectors 1272 than an opposite second or upper side 1264. As best seen in FIG. 13D, the distal end 1256 is offset such that the first side 1263 is closer to the flanged connectors 1272 than the second side 1264. Similarly, the bore 1260 and/or the recess 1261 in the inlet end 1254 may also be offset from the central axis 1218. It will be appreciated that the construction of the serial valve may allow the bore 1260 and/or the recess 1261 to be substantially offset from the central axis 1218, even to the point of overlapping with the wall of the first and/or second hub portions of a hub to which the valve is attached. It will be further appreciated that the inlet and outlet ends 1254, 1256 do not need to be offset by the same degree and consequently may have different shapes relative to one another. Such offset may facilitate slitting the valve body 1252 during use, as described elsewhere herein. Alternatively, as shown in FIG. 17A, the valve body 1252' may be located substantially concentrically around the central axis 1218.'

Figure 17B:
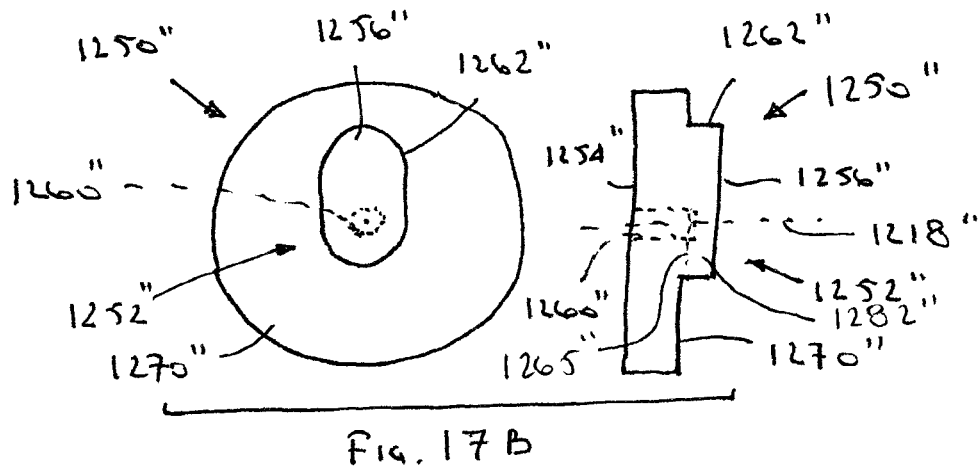
Figure 17C:
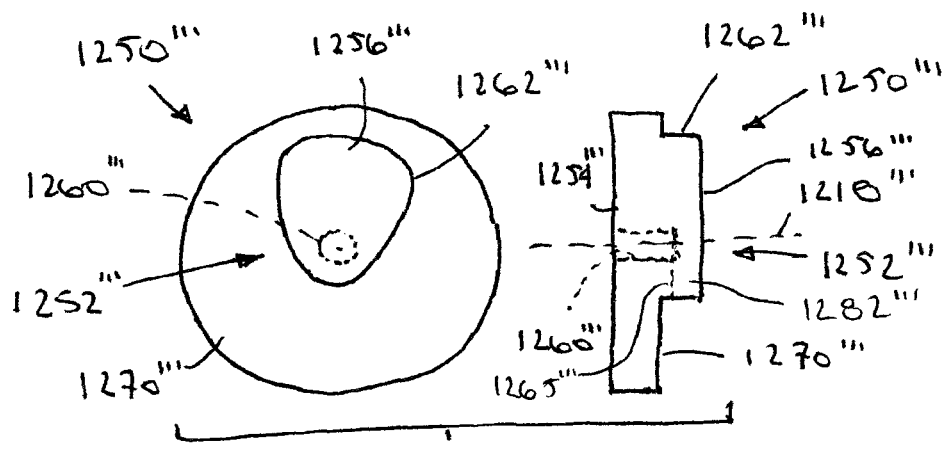

It will be appreciated that the outlet end 1256 or the entire valve body 1252, and consequently the cover 1282, may have other shapes instead of a substantially circular shape, e.g., concentric with or offset from the central axis. For example, as shown in FIG. 17B, a valve body 1252" may be provided that has an elliptical or other oblong-shaped outlet end 1256", e.g., offset from a central longitudinal axis 1218." For example, one end of the oblong-shape valve body 1252" may be disposed intersecting or otherwise adjacent the central axis 1218" and/or bore 1260." In another alternative, shown in FIG. 17C, a valve body 1252''' may be provided that has a tear-shaped outlet end 1256''', e.g., offset from a central longitudinal axis 1218.''' For example, a relatively narrow tip of the tear-shape may be disposed adjacent the central axis 1218''' and/or bore 1260,''' and a wider base of the tear-shape may be disposed further from the central axis 1218.''' In this alternative, the wider base may enhance support of the cover 1282''' when the slit 1265''' is formed, as described further below, which may reduce the risk of the cover 1282''' prolapsing into the bore 1260.''' In other alternatives, the outlet end or the entire valve body may have various other shapes, such as a substantially triangular shape, polygonal shape, and the like (not shown).

Figure 19:
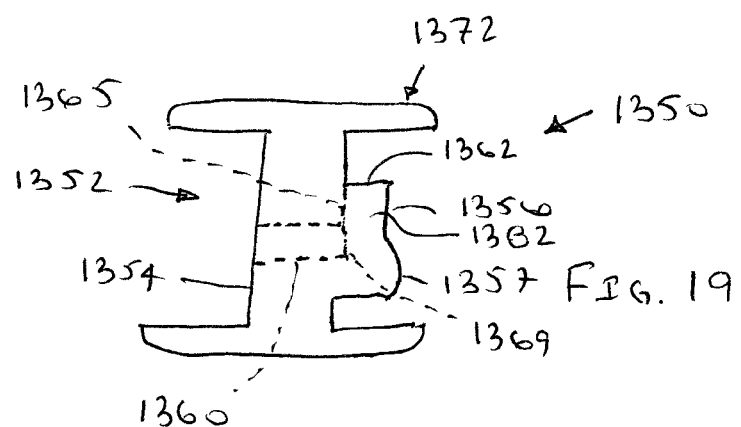
FIG. 19 is a cross-sectional view of another embodiment of a valve including a valve body and flanges connectors extending from an outer periphery of the valve body, an outlet end of the valve body including a thicker region for support a cover sealing a bore of the valve body.

Further, while the outlet end 1256 of the valve body 1252 of FIGS. 13A-13D is generally depicted as having a substantially planar distal surface, alternatively, the outlet end may have other shaped surfaces, such as a convex surface (e.g., similar to the valve 50' shown in FIG. 2D), a concave surface, or other non-planar surface (not shown). For example, as shown in FIG. 19, the outlet end 1356 of a valve body 1352 may have a variable thickness, e.g., to provide desired properties for the cover 1382 created when the slit 1365 is cut into the valve body 1352. In the embodiment shown, the outlet end 1356 has a relatively thicker region 1357 opposite the slit 1365, e.g., which may provide additional support adjacent the base 1369 of the slit 1365. Such support may enhance the bias of the cover 1382 to return towards the inlet end 1354 to substantially seal the bore 1360.

In addition or alternatively, as shown in FIG. 13B, the outlet end 1256 of the valve body 1252 may include a pair of opposing supports or wings 1258, e.g., providing stops for the valve 1250 that prevent tearing of the valve body 1252, e.g., during opening and closing the cover 1282, as described further below. For example, the stops 1258 may be located symmetrically relative to one another closer to the upper side 1264 of the valve body 1252 than the lower side 1263, e.g., to define a generally T shape for the second end 1256. The stops 1258 may define stop surfaces 1259, e.g., defining an acute angle with the adjacent outer surface 1262, which may resist tearing and/or otherwise enhance the durability of the valve body 1252 during use, as described further below.

Figure 16:
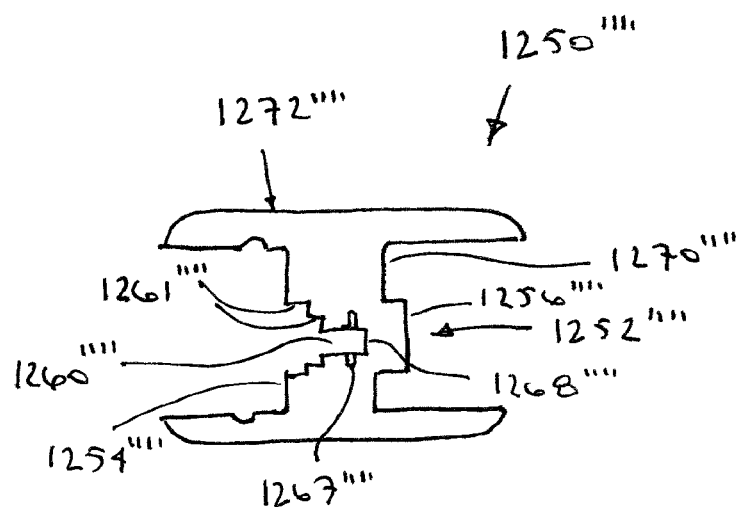
FIG. 16 is a cross-sectional view of an alternative embodiment of a valve, similar to the valve of FIGS. 13A and 13B, including multiple inlet recesses and a bore recess.

The bore or passage 1260 extends from the inlet end 1254 of the valve body 1252 at least partially towards the outlet end 1256, e.g., substantially parallel to the central axis 1218. For example, the bore 1260 may extend from the inlet end 1254 partially through the valve body 1252 to an intermediate region such that the bore 1260 defines a bottom surface 1268 spaced proximally from the outlet end 1256, as best seen in FIGS. 13C and 13D. Optionally, a recess may be provided within the bore 1260, e.g., for receiving lubricant or other desired material (not shown). For example, as shown in FIG. 16, an annular recess 1267' may be provided within the bore 1260," e.g., adjacent the bottom surface 1268' of the bore 1260," similar to other embodiments herein.

Optionally, the inlet end 1254 may include a transition, e.g., to guide or otherwise facilitate introducing an instrument (not shown) into the bore 1260. For example, as shown in FIG. 13A, the inlet end 1254 of the valve body 1252 may be offset distally from the valve support 1270 to define a circular or other recess 1261 in the inlet end 1254 that surrounds the bore 1260. It will be appreciated that the inlet and outlet ends 1254, 1256 may be offset axially from the valve support 1270 by different distances, e.g., such that the recess 1261 and outer surface 1262 may have different axial depth or length dimensions. Alternatively, as shown in FIG. 16, a plurality of stepped recesses 1261' may be provided that transition from the inlet end 1254' to the bore 1260." In further alternatives, a tapered, conical, funnel-shaped, or other recess may be provided that communicates with the bore 1260, e.g., a funnel-shaped transition, as shown in FIGS. 18A-18D.

As shown in FIGS. 14A-14D and 15A-15C, the slit 1265 may extend through the valve body 1252 to at least partially intersect the bore 1260 adjacent the outlet end 1256 to define a flap or cover 1282, which may be resiliently directed away from the inlet end 1254, e.g., to open and close the bore 1260, as described further below. For example, the bore 1260 may allow the valve 1250 to provide a substantially fluid-tight seal when a medical device or other instrument (not shown) is inserted into the bore 1260 through the valve body 1252, similar to other embodiments herein, while the cover 1280 may provide a fluid-tight seal when the bore 1260 is empty (i.e., without an instrument inserted into the bore 1260).

Figure 14A:
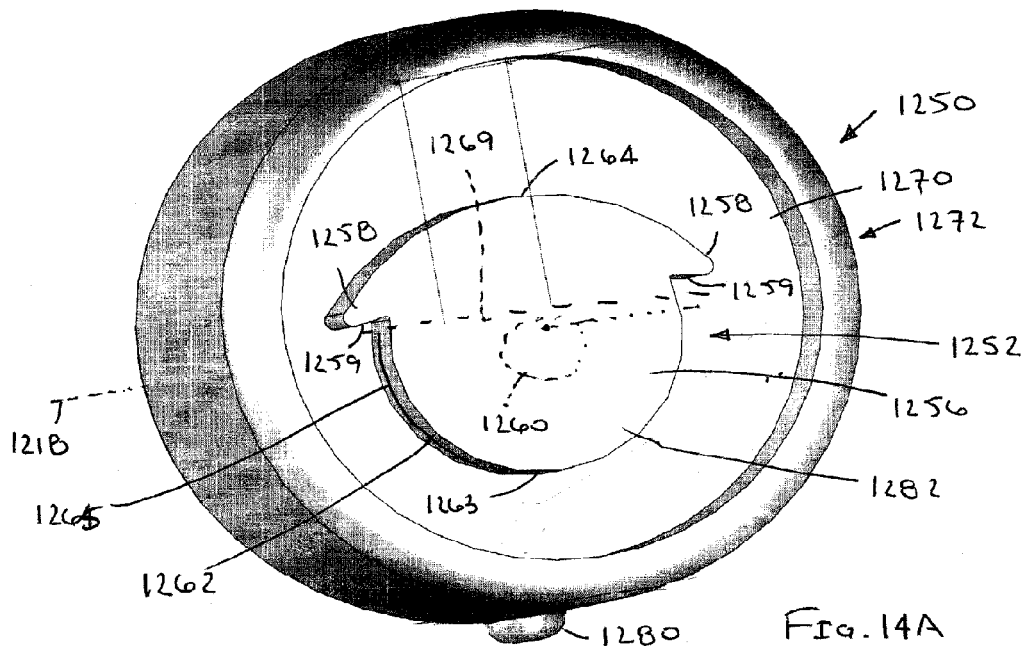
FIGS. 14A-14D are perspective views of the valve of FIGS. 13A and 13B taken from the outlet end, showing alternative configurations for slits that may be created transversely through the valve body to create a flap for resiliently sealing a bore through the valve body.

As shown in FIGS. 14A-14D, the slit 1265 may extend partially through the valve body 1252 transversely to the central axis 1218, e.g., from the lower side 1263 of the outer surface 1262 towards the opposite upper side of the outer surface 1262, i.e., towards the stops 1258. As shown in FIG. 14A, the slit 1265 may extend from the lower side 1263 and terminate in a substantially straight base 1269 that extends generally between the stops 1258, e.g., such that the slit 1265 extends from the lower side 1263 past the central longitudinal axis 1218 and the bore 1260. Alternatively, if the bore is offset laterally from the central axis 1218, the slit 1265 may not extend past the central axis 1218 as long as the slit 1265 partially or fully intersects the bore 1260. As shown in FIG. 14A, the base 1269 of the slit 1265 terminates adjacent the stops 1258 without penetrating into the stop surfaces 1259.

Figure 14B:
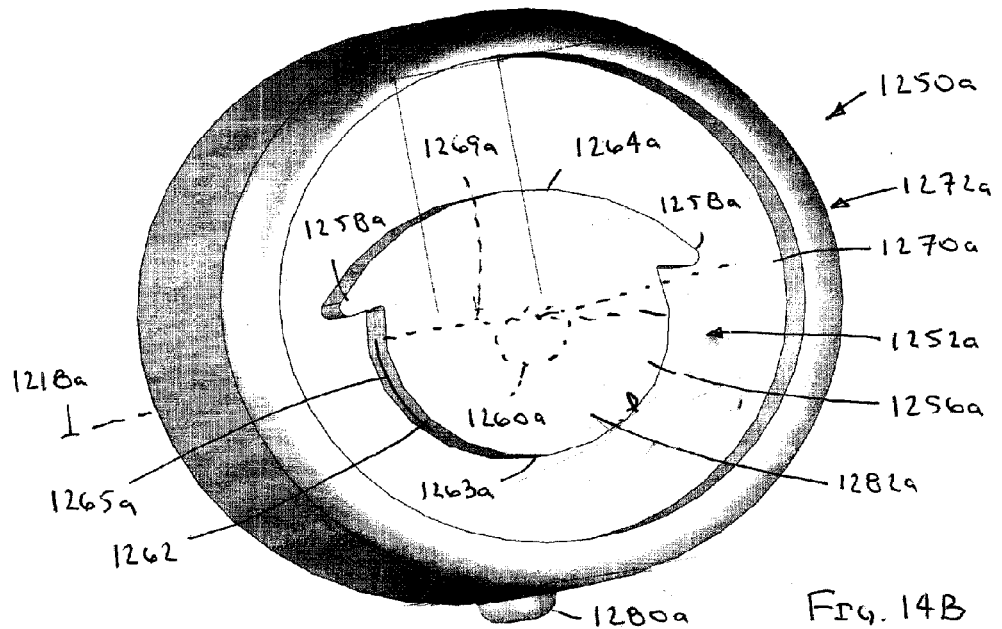

Alternatively, as shown in FIG. 14B, a slit 1265a may be provided that extends from the lower side 1263a to intersect the bore 1260a (possibly but not necessarily extending past a central longitudinal axis 1218a and/or entirely past the bore 1260a) and terminates in a substantially straight base 1269a that intersects bore 1260a. In this alternative, the base 1269a of the slit 1265a is disposed immediately adjacent the bore 1260a, i.e., closer than the base 1269 of the slit 1265 shown in FIG. 14A. This configuration may enhance support of the cover 1282a, which may reduce the risk of the cover 1282a "prolapsing," i.e., folding or otherwise entering and/or remaining in the bore 1260a, which may interfere with introducing an instrument through the bore 1260a and/or cause leakage through the valve 1250a when no instrument present in the bore 1260a.

Figure 14C:
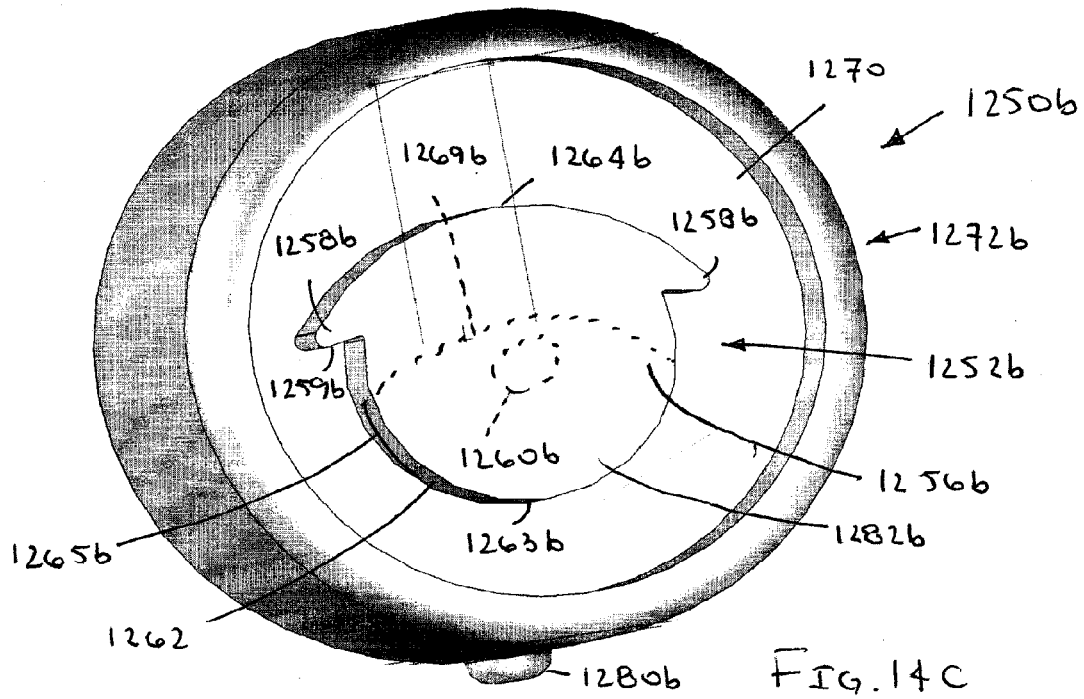
Figure 14D:
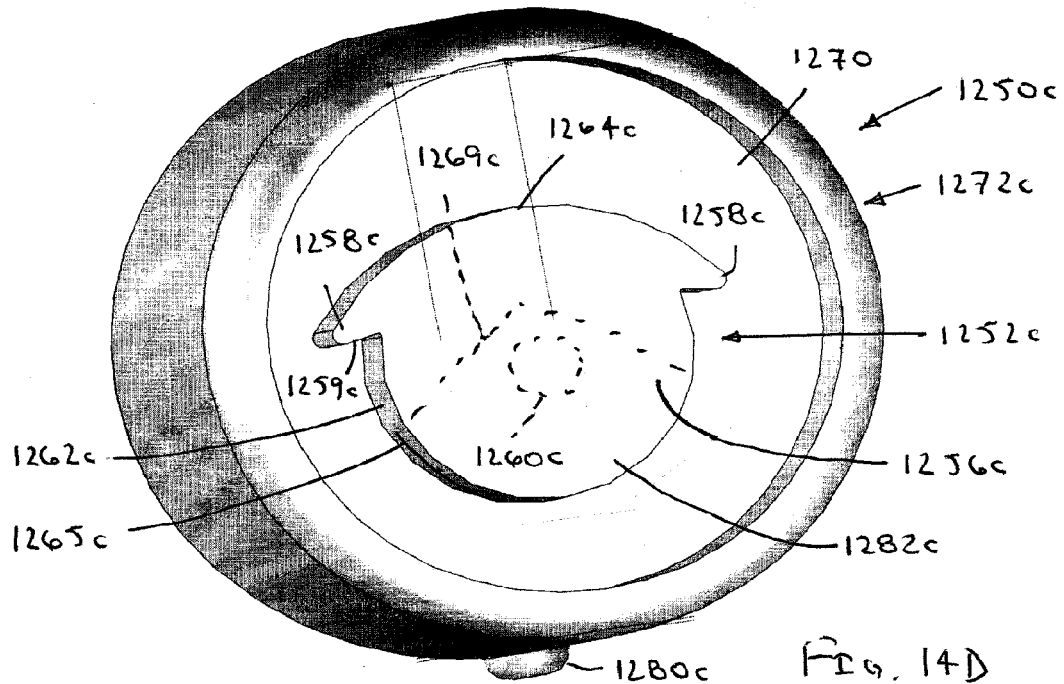

In another alternative shown in FIG. 14C, a slit 1265b may be provided that terminates in a base 1269b defining an arc of a circle or other curved line, e.g., such that the slit 1265b intersects the bore 1260b (and possibly extends past a central longitudinal axis 1218b and/or the bore 1260b). In this alternative, the base 1269b may provide a support for the cover 1282b that partially surrounds the bore 1260b, thereby further supporting the cover 1282b and/or reducing the risk of prolapse. In yet another alternative shown in FIG. 14D, a slit 1265c may be provided that terminates in a base 1269c defining a "V" shape, e.g., such that the slit 1265c intersects the bore 1260c (and again, possibly extends past a central longitudinal axis 1218c). Thus, similar to the cover 1282b, the base 1269c of the slit 1265c may provide a support that partially surrounds the cover 1282c.

Figures 20A, 20B:
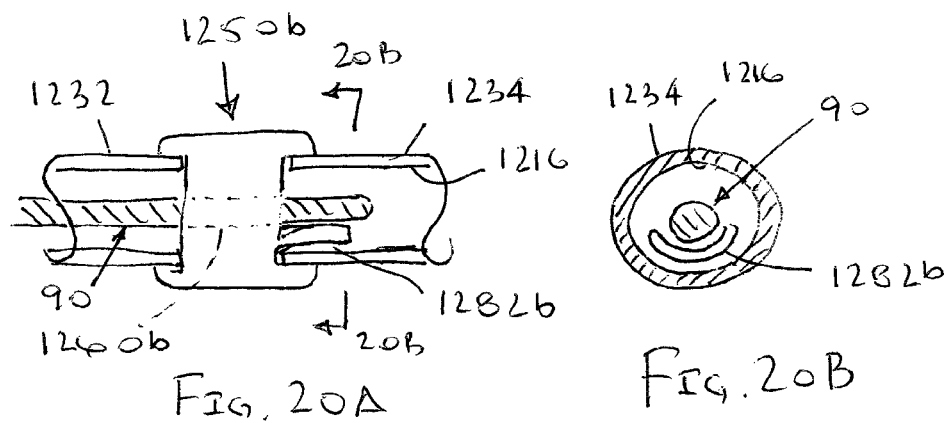
FIG. 20A is a partial cross-sectional side view of a valve secured between hub portions of a hub, with an instrument introduced through the valve.
FIG. 20B is a cross-section of the valve and hub taken along line 20B-20B.

In these embodiments, the resulting support may cause the cover 1282b, 1282c to deform rather than simply hinge. For example, as shown in FIGS. 20A and 20B, when an instrument 90 is introduced through the bore 1260b and pushes the cover 1282b out of the way to exit the bore 1260b, the cover 1282b may adopt a generally "U" shape as it deforms out of the way of the instrument, rather than simply bending at a hinge point. This may reduce the risk of prolapse and/or may enhance the resiliency of the cover 1282b to return back to seal the bore 1260b when the instrument 90 is removed. Likewise, in other embodiments where the base 1269 of the slit 1265 intersects the path of an instrument passing through the bore 1260 (e.g., where the base 1269 intersects the bore 1260 before or after the bore 1260 is expanded by the instrument), passage of the instrument through the bore 1260 may cause the cover 1282 to deform, e.g., into a "U" shape, rather than simply hinge.

Thus, with reference to FIG. 14A (although applicable to the other embodiments herein), the stops 1258 may support the cover 1282, e.g., to ensure that the cover 1282 is biased to return towards the bore 1260 to substantially seal the bore 1260, yet may be resiliently directed away from the bore 1260 to accommodate an instrument (not shown) passing through the bore 1260. In addition, the stop surfaces 1259 may support the cover 1282 to prevent the slit 1265 from propagating, e.g., through to the second side 1264 of the valve body 1252, which otherwise may cause the cover 1282 to tear off or cease to close properly. For example, when the cover 1282 is opened or otherwise bent away from the bore 1260, there is a chance that the material of the valve body 1252 may tear and propagate the slit 1265 further towards the second side 1264 of the valve body 1252. The acute angle of the stop surfaces 1259 may resist such propagation, thereby ensuring the cover 1282 remains substantially integral with the valve body 1252.

Figure 15A:
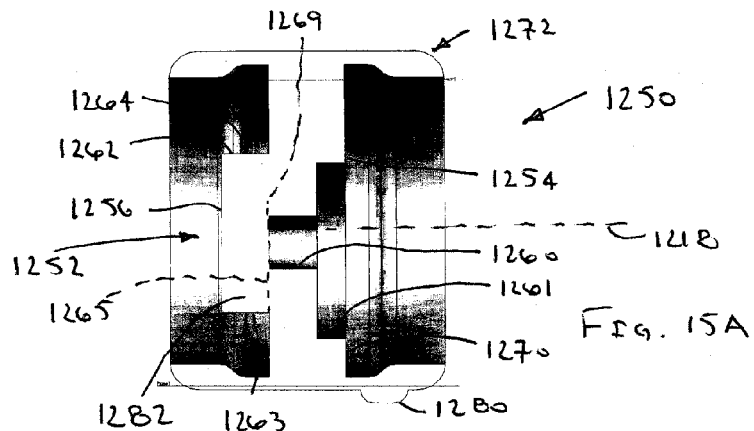
FIGS. 15A-15C are cross-sectional views of the valve of FIGS. 13A and 13B, showing additional alternative configurations for slits that may be created transversely through the valve body to create a flap for resiliently sealing a bore through the valve body.
Figure 15B:
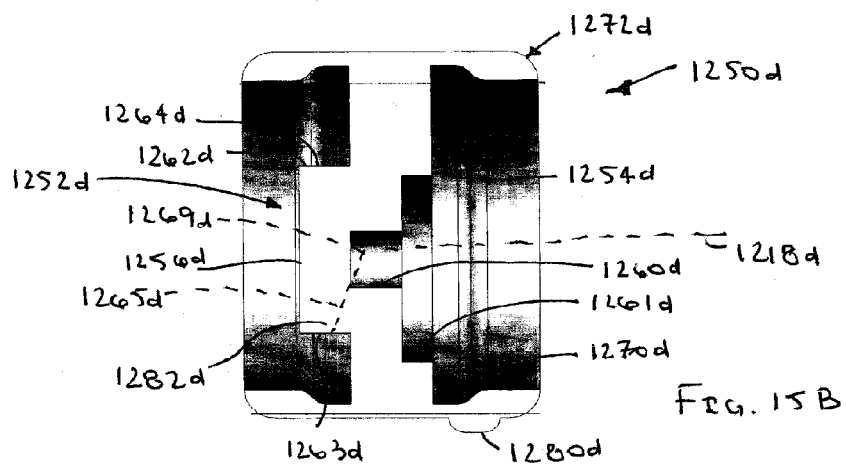
Figure 15C:
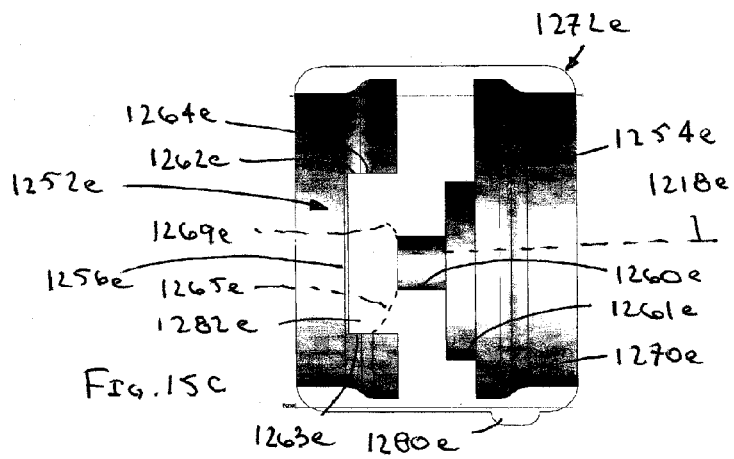

Turning to FIGS. 15A-15C, the slit 1265 may lie within a plane or may have a more complicated three-dimensional shape as long as the slit 1265 at least partially intersects the bore 1260 to provide a cover 1282 that may be resiliently directed away from the bore 1260. For example, as shown in FIG. 15A, the slit 1265 lies within a plane that extends substantially perpendicular to the central axis 1218. Thus, in this embodiment, the cover 1282 may have a substantially uniform thickness between the lower side 1263 and the base 1269 of the slit 1265. As shown, the slit 1264 may be aligned substantially with the bottom 1268 of the bore 1260, although alternatively the slit 1265 may intersect the bore 1260 adjacent the bottom 1268, such that the flap 1282 includes a recess therein (not shown).

Alternatively, as shown in FIG. 15B, a slit 1265d may be created that lies within a plane that intersects a central longitudinal axis 1218d at a non-perpendicular angle, e.g., an acute or obtuse angle relative to the central axis 1218d as measured from the inlet end 1254*d*. For example, as shown, the cover 1282*d* may have a tapered thickness, e.g., relatively thinner adjacent the lower side 1263*d* and relatively thicker adjacent the bore 1260*d*. In a further alternative, shown in FIG. 15C, a slit 1265*e* may be provided that has a curved shape, e.g., defining a substantially constant or variable radius arc. As shown, the resulting cover 1282*e* may be thinner adjacent the lower side 1263*e* and the base 1269*e* of the slit 1265*e* than at an intermediate region therebetween. In other alternatives, multiple slits (not shown) may be created in any of the valve bodies, if desired, to create a cover or flap that opens sufficiently to accommodate an instrument being received therethrough, while resiliently sealing the bore.

In any of these embodiments, the resulting cover, such as the cover 1282 shown in FIGS. 14A and 15A, may have a thickness coextensive with the length of the outer surface 1262 of the valve body 1252. Alternatively, the slit 1265 may be created at an intermediate location in the outer surface 1262 such that the thickness of the cover 1282 is less than the length of the outer surface 1262. For example, a relatively thinner cover may be more flexible and consequently may increase the risk of prolapse compared to a relatively thicker cover. However, if the cover 1282 is too thick, then the cover 1282 may increase friction when an instrument (not shown) is introduced through the bore 1260 and deforms and/or pushes the cover 1282 out of the way. Thus, it may be desirable that the thickness of the deformed cover 1282 is not generally greater than the annular space present when a device (not shown) passes through the bore 1260 and distally into the lumen 1216 of a hub 1230 to which the valve 1250 is attached, for example, the lumen 1216*b* of the second hub portion 1234 of the hub 1230 shown in FIG. 12A.

Additionally, the width, height, and/or other cross-section of the cover 1282 may be selected to reduce the risk of the cover 1282 prolapsing into the bore 1260 during use.

In addition, it may be desirable that a height and/or width of the cover 1282 may be substantially smaller than the outer dimensions of the valve 1250 and/or the lumen 1216*b* of the hub 1230, e.g., to reduce the risk of interference between the cover 1282 and the wall of the hub 1230, which may otherwise prevent the cover 1282 from resiliently closing, and/or to reduce friction between the cover 1282 and an instrument introduced through the bore 1260. For example, as shown in FIGS. 14A and 15A, the height and/or width of the outlet end 1256 of the valve body 1252 substantially perpendicular to the central axis 1218 may be substantially smaller than the inner diameter of the flanged connectors 1272, and, consequently, smaller than the inner diameter of hub portions, not shown, to which the valve 1250 is secured. Thus, the resulting cover 1282 may also have a height and/or width substantially smaller than the inner diameter of hub portions to which the valve 1250 is secured.

In an alternative embodiment, the outer surface 1262 of the valve body 1252 may be stepped down immediately adjacent the outlet end 1256 from an adjacent outer surface (not shown) between the outlet end 1256 and the inlet end 1254. A slit may be created through the stepped down region to reduce the height of the resulting cover (not shown) relative to the rest of the outlet end of the valve.

Returning to FIGS. 13A-13D, the valve support 1270 and flanged connectors 1272 may support the valve body 1252 within a hub (not shown), e.g., when the valve 1250 is secured between hub portions 1232, 1234 of the hub 1230 shown in FIGS. 12A and 12B, as described further below. The valve support 1270 may be a substantially planar member extending radially outwardly from the valve body 1252, e.g., to define a substantially circular or other outer shape similar to the shape of a hub to which the valve 1250 is coupled. The valve support 1270 may be sufficiently flexible to support the valve body 1252 within a hub while allowing the valve body 1252 to expand, e.g., if necessary to accommodate introducing an instrument (not shown) through the bore 1260.

As shown, the valve support 1270 may have a substantially uniform thickness, although alternatively, the valve support 1270 may have a variable thickness (not shown), if desired. As best seen in FIGS. 13A and 13D, the valve support 1270 may include a first or proximal surface 1270*i* that is substantially flush with the first end 1254 of the valve body 1252, although alternatively, the valve support 1270 may be offset from the first end 1254 of the valve body 1252, if desired (not shown). As best seen in FIGS. 13B-13D, the valve support 1270 may include a second or distal surface 1270*ii* that is offset from the second end 1256 of the valve body 1252, e.g., with the outer surface 1262 of the valve body 1252 extending between the second end 1256 and the distal surface 1270*ii*.

With continued reference to FIGS. 13A-13E, the flanged connectors 1272 include opposing annular bodies extending from the outer region of the valve support 1270 away from one another, e.g., substantially parallel and concentrically around the central axis 1218 of the valve 1250. Alternatively, the inlet side of the valve body may extend radially outwardly to the flanged connectors, e.g., with the outlet end providing the outer surface for the cover, and the valve support may be omitted. As best seen in FIGS. 13C and 13D, the flanged connectors 1272 may include inner annular recesses 1274, e.g., adjacent the valve support 1270 and spaced apart from ends 1276 of the flanged connectors 1272. As described further below, the recesses 1274 may enhance flexibility of the flanged connectors 1272 and/or provide pockets for receiving adhesive or other bonding or sealing materials.

Optionally, as shown in FIGS. 13A-13E, the valve 1250 may include one or more raised features or other markers 1280, e.g., on an outer surface of one or both of the flanged connectors 1272. As shown, a marker 1280 is provided at a circumferential location corresponding to the lower side 1263 of the valve body 1250, e.g., where the valve body 1252 is closer to the flanged connectors 1272 and/or the closest to the open side of the cover 1282. The marker(s) 1280 may facilitate proper orientation of the valve 1250 when being coupled to a hub, as described further below.

One or more of the components of the valve 1250 may be formed from an elastomeric material, such as silicone, chronoprene, isoprene, santoprene, and the like. In one embodiment, the valve body 1252, valve support 1270, and flanged connectors 1272 may be integrally formed as a single piece, e.g., by injection molding, casting, and the like. The bore 1260, recess 1261, and/or other features of the valve body 1252 may be integrally formed with the valve body 1252, or, alternatively, the valve body 1252 may be formed as a solid body and the features may be formed into the solid body, e.g., by cutting, coring, machining, and the like. Similarly, the marker(s) 1280 may be integrally formed with the flanged connectors 1272 or may be attached to the flanged connectors 1272 after they are formed. In alternative embodiments, one or more components of the valve 1250 may be formed separately and then attached together. For example, the flanged connectors 1272 may be formed separately from the valve body 1252 and valve support 1270 and then attached together, e.g., by bonding with adhesive, fusing, sonic welding, and the like. Similarly, a disc or other member for the cover 1282 may be formed separately from the rest of the valve body 1252 (not shown), and then the member may be attached to the valve body 1252, e.g., by bonding with adhesive, fusing, sonic welding, and the like, to provide the cover 1282.

Figure 18A:
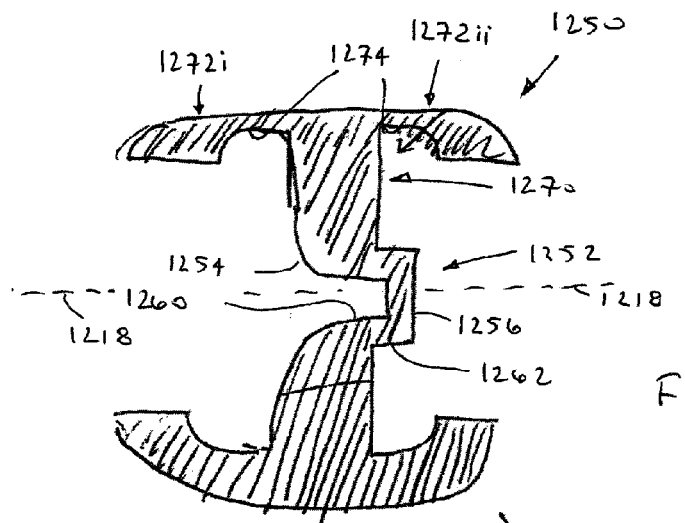
FIGS. 18A-18D are cross-sectional views of a valve, similar to the valve of FIGS. 13A and 13B, showing the flanged connectors being inverted to facilitate cutting a slit in the valve body to create a valve body and to facilitate bonding the valve to a hub.
Figure 18C:
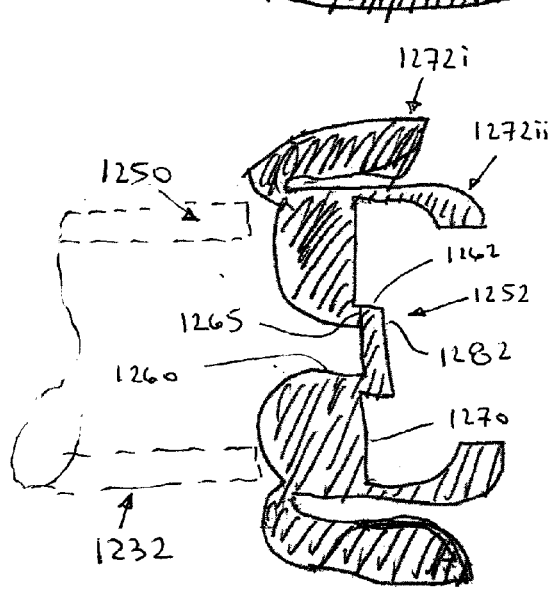
Figure 18B:
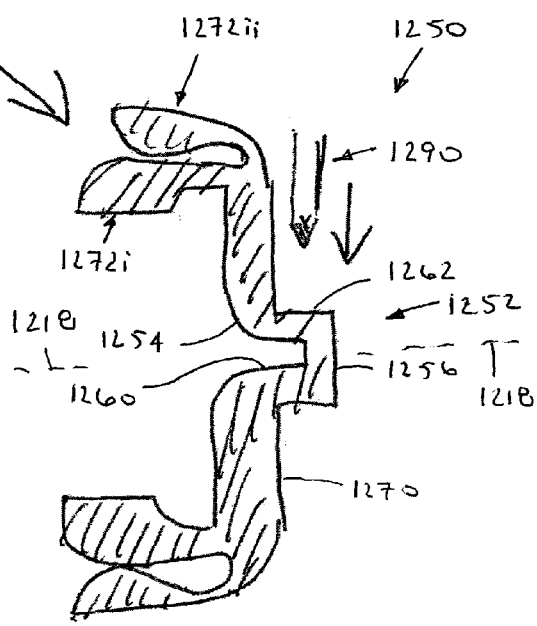

Turning to FIGS. 18A and 18B, an exemplary method is shown for creating a slit 1265 and cover 1282 in the valve body 1252, e.g., as shown in FIGS. 14A and 15A. For example, FIG. 18A shows an exemplary embodiment of a valve 1250 including a valve body 1252, a valve support 1270, and proximal and distal flanged connectors 1272i, 1272ii, which may be similar to any of the embodiments described elsewhere herein. As shown, the components of the valve 1250 are formed as a single, integral piece but without a slit or cover in the valve body 1252. As can be seen, the distal flanged connector 1272ii surrounds the second end 1256 of the valve body 1252, which may make it difficult to access the outer surface 1262 of the valve body 1252 to create a slit.

Turning to FIG. 18B, the flanged connector 1272ii surrounding the second end 1256 of the valve body 1252 may be folded or inverted over the proximal flanged connector 1272i, e.g., to facilitate accessing the outer surface 1262. Because of the recess 1274, the flanged connector 1272ii has a relatively thin-walled region immediately adjacent the valve support 1270, which may enhance the flexibility of the flanged connector 1272ii, e.g., to facilitate inverting and/or maintaining inversion of the flanged connector 1272ii as shown.

A blade or other cutting element 1290 may then be used to create the slit 1265 (not shown, see, e.g., FIGS. 14A, 15A) that extends transversely from the outer surface 1262 partially through the valve body 1252, e.g., substantially perpendicular to the central axis 1218, as shown. For example, the cutting element 1290 may be a substantially flat blade including a sharpened leading edge that may cut through the material of the valve body 1252 to create a slit 1265 having a substantially straight base 1269, thereby resulting in a cover 1282 (also not shown, see, e.g., FIGS. 14A, 15A). Alternatively, other shaped cutting elements or devices may be used, for example, a heated blade, wire, or other element (not shown) that may melt through the valve body 1252, e.g., in addition to or instead of mechanically cutting the valve body 1252, similar to other embodiments herein.

Figure 18D:
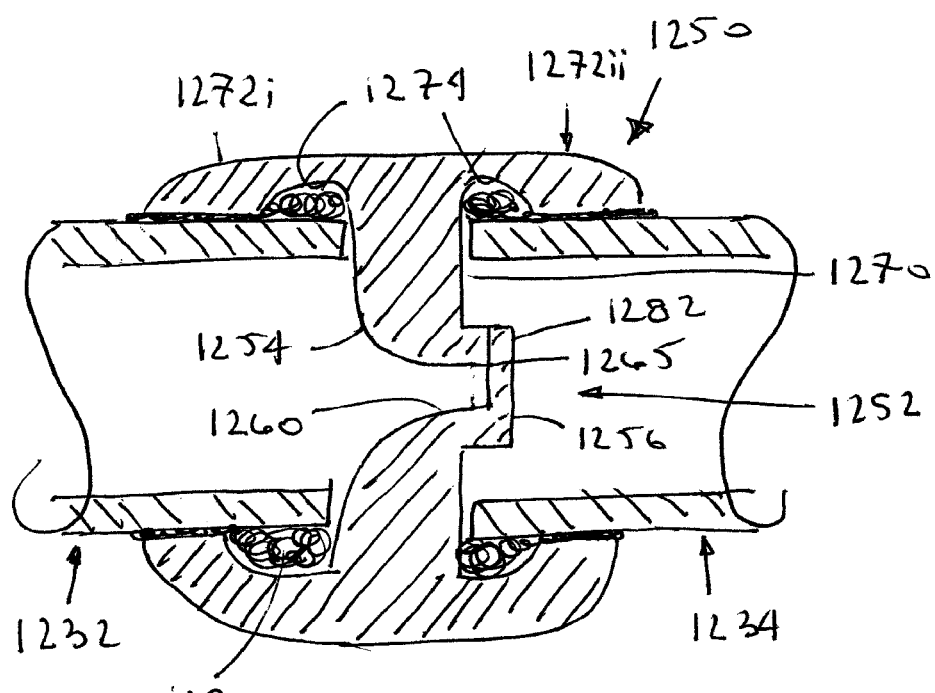

Once the slit 1265 and cover 1282 are formed, the flanged connector 1272ii may be returned back to its original orientation surrounding the second end 1256 of the valve body 1252, as shown in FIGS. 18A and 18C. During assembly, e.g., when the valve 1250 is being secured to a hub, either flanged connector 1272 may be inverted, e.g., as shown in FIG. 18C, to facilitate positioning the valve 1250 within a gap between hub portions of a hub (only hub portion 1232 shown), such as the hub 1230 of FIGS. 12A and 12B. The flanged connector(s) 1272 may be sufficiently flexible to be inverted for positioning, and then be returned to its original orientation, consequently capturing the adjacent hub portions 1232, 1234 within the flanged connectors 1272, as shown in FIG. 18D, and described further below.

Returning to FIGS. 1A and 1B, any of the valves herein, such as valve 50 or 50,' may be secured to a hub 30 of an apparatus 10, e.g., a sheath, catheter, or other tubular member, to accommodate receiving one or more devices, e.g., a catheter, lead, guidewire or other medical device (not shown), through the hub 30 and into the lumen 16 of the tubular body 11, while providing a substantially fluid-tight seal. For example, as described above, a hub 30 may be formed that includes a first hub portion 32 and a second hub portion 34 coupled together by hub arm 36 such that first and second hub lumens 32c, 34c of the hub portions 32, 34 are aligned with one another and the hub portions 32, 34 are spaced apart from one another to define a gap 35, as best seen in FIG. 1B.

A valve 50 may be selected and secured to the hub 30 within the gap 35. For example, using any of the methods described above, a valve 50 may be formed that includes a valve body 52 including a valve passage 60 extending therethrough. During manufacturing or final assembly, the valve body 52 may be secured within the gap 35 between the first and second hub portions 32, 34 such that the valve passage 60 is aligned with the hub lumens 32c, 34c, e.g., to accommodate receiving a medical device through the hub 30 into the tubular body 11 while providing a substantially fluid tight seal.

Alternatively, it may be possible to provide a plurality of valves to an end user separate from a hub 30 such that the user may select a desired valve for use during a particular procedure. For example, different valves having different configurations, e.g., different sizes of valve passage 50, different material properties, and the like, may be provided to a user, and the user may simply select a desired configuration from the available valves and secure the valve to the hub 30.

For example, as described above, the first and second hub portions 32, 34 may be directed away from one another, e.g., by bending the hub arm 36 slightly, to increate a length of the gap 35, thereby providing additional space to insert the valve body 52 between the hub portions 32, 34. In one embodiment, the hub arm 36 may be bent along the longitudinal axis 18, e.g., such that the first and second hub portions 32 remain generally aligned with one another but the distance between them is increased. In addition or alternatively, the hub arm 36 may be bent transversely relative to the longitudinal axis 18, e.g., such that the first and second hub portions 32 are directed off the longitudinal axis 18, e.g., on opposite sides.

The valve body 52 may then be inserted within the gap 35 between the hub portions 32, 34, and the hub portions 32, 34 may be directed back towards one another to capture the valve body 52 between the hub portions 32, 34. In one embodiment, the hub portions 32, 34 may be directed towards one another simply by releasing the hub arm 36 and/or the hub portions 32, 34, whereupon the hub arm 36 may resiliently return towards its original shape, thereby directing the hub portions 32, 34 towards one another.

Figure 5A:
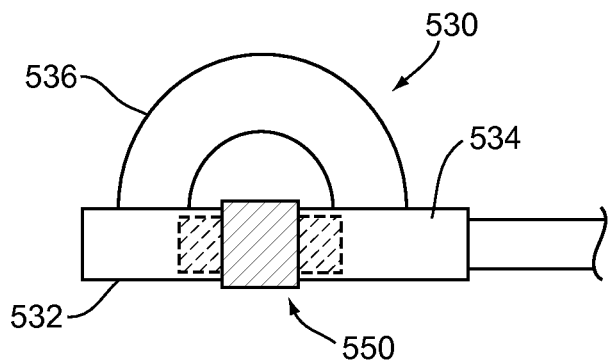
FIG. 5A is a side view of another exemplary embodiment of a hub including a valve coupled to the hub that includes undersized flanged connectors.
Figure 5B:
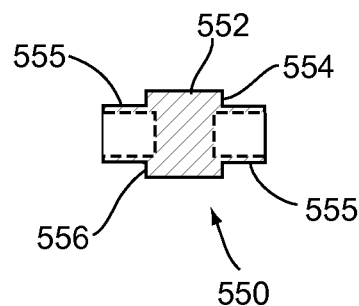
FIG. 5B is a side view detail of the valve of FIG. 5A.
Figure 6A:
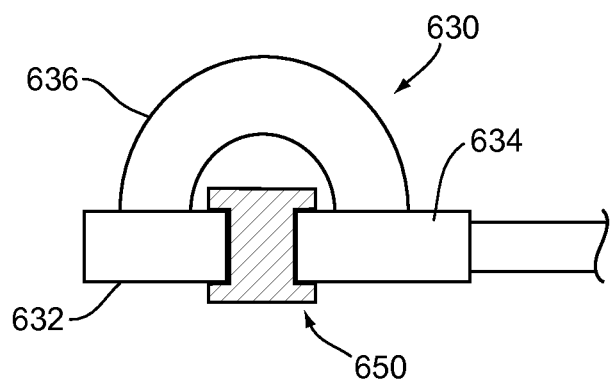
FIG. 6A is a side view of still another exemplary embodiment of a hub including a valve coupled to the hub that includes oversized flanged connectors.
Figure 6B:
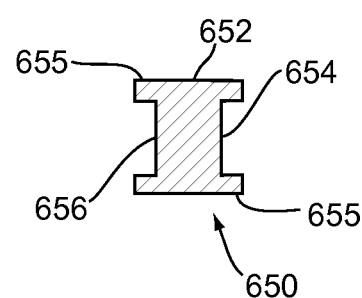
FIG. 6B is a side view detail of the valve of FIG. 5A.

The resulting interference fit alone may be sufficient to secure the valve 50 within the gap 35. For example, as shown in FIG. 3, when the valve 50 is captured between the hub portions 32, 34, the beveled edges 32d, 34d may engage the slots 58 in the valve body 52, thereby substantially securing the valve 50 within the gap 35. In an alternative embodiment, shown in FIGS. 5A and 5B, a valve 550 may be provided that includes flanged connectors or tubular extensions 555 on one or both ends 554, 556 of a valve body 552, which may formed similar to any of the embodiments herein. As shown in FIG. 5B, the tubular extensions 555 may be "undersized," i.e., smaller than the corresponding hub portions 532, 534 between the valve 550 is secured, e.g., such that the tubular extensions 555 may be received in the lumens of the hub portions 532, 534. Alternatively, as shown in FIGS. 6A and 6B, a valve 650 may be provided that includes flanged connectors or tubular extensions 655 on one or both ends 654, 656 of a valve body 652 that may be "oversized," i.e., larger than corresponding hub portions 632, 634, e.g., similar to the valve 1250 of FIGS. 13A-13E. Thus, in this alternative, the tubular extensions 655 may extend over a portion of the respective hub portions 632, 634 to provide an interference fit. In these alternatives, the tubular extensions 555, 655 may have lengths sufficient to substantially seal the valve 550, 650 between the hub portions, e.g., between about 0.5 and three millimeters (0.5-3 mm). In addition or alternatively, the tubular extensions 555, 655 may be attached to the hub portions, e.g., by bonding with adhesive, fusing, sonic welding, and the like. It will be appreciated that, in embodiments of the serial valve where no connectors extend inside the lumens of the corresponding hub portions, greater luminal working space may be available for any given starting luminal diameter.

If desired, in addition or alternatively, the valve body 52 may be secured using other methods, e.g., at least one of bonding with adhesive, welding, insertion molding, or fusing the valve body 52 to the first and/or second hub portions 32, 34, surrounding bands (not shown), and/or other connectors. Where adhesive is used to secure the valve 50 within the gap 35, the valve body 52 and/or the hub portions 32, 34 may include recesses, channels, or other features (not shown) designed to receive and/or distribute adhesive at the interface between the hub portions 32, 34 and the valve body 52.

For example, with reference to FIG. 18A-18D, the valve 1250 may include annular recesses 1274 within flanged connectors 1272 adjacent the valve support 1270. The recesses 1274 may provide pockets within which adhesive may be placed before coupling the valve 1250 to a hub (not shown) or within which adhesive placed on the hub portions 1232, 1234 of a hub may flow. For example, FIG. 18D shows the recesses 1274 substantially filled with adhesive 1291, which may enhance bonding the valve 1250 between the hub portions 1232, 1234, e.g., as shown in FIGS. 12A and 12B.

Returning to FIGS. 1A and 1B, if the hub portions 32, 34 include relatively thin walled regions and/or the valve 50 includes a valve passage offset towards one side of the valve body 52, one or more connectors or alignment features may be provided on the valve 50 and/or hub portions 32, 34 to ensure that the valve 50 is properly oriented when captured within the gap 35. For example, one of the hub portions 32, 34 and the valve body 52 may include one or more tabs (not shown) that may be received in corresponding one or more slots (also not shown) in the other of the hub portions 32, 34 and the valve body 52 only when the valve 50 is oriented properly relative to the hub portions 32, 34. Such alignment features may ensure that relatively thin walled regions of the hub portions 32, 34 are aligned with the thinner region of the valve body 52, which may facilitate slitting the hub 30 after use during a procedure, as described further below.

Alternatively, as shown in FIGS. 12A-12B and FIGS. 13A-13E, a valve 1250 may include a visible marker 1280 identifying the side of the valve 1250 towards which the valve body 1252 is offset. Thus, when the valve 1250 is secured between the hub portions 1232, 1234, the marker 1280 may be oriented to align the valve body 1252 within the hub 1230, e.g., to ensure that the thinnest portion of the valve support 1270 is aligned with a desired slittable region of the hub 1230, as described elsewhere herein. In addition or alternatively, the marker 1280 may be provided opposite the base 1269 of the slit 1265 such that the orientation of the cover 1282 may also be identified by the marker 1280, if desired. Knowing this orientation may also facilitate slitting the valve 1250 after use since a slitter (not shown) introduced into the hub may enter the bore 1260 and open the cover 1282 at the free end of the cover 1282 rather than at the base 1269 of the slit 1265, as described elsewhere herein. Likewise, the valve 1250 may be attached to the hub 1230 such that the free end of the cover 1282 is oriented toward, and the base 1269 of the slit 1265 is oriented away from the wall of the hub 1230 that is intended for slitting. Thus, the slitter (not shown) may enter the bore 1260, open the cover 1282, and cut the valve without cutting through the base of the slit 1265.

In an alternative embodiment, one of the first and second hub portions 32, 34 may be provided separate from the hub arm 36, e.g., during manufacturing, and the valve 50 may be secured to the hub 30 before attaching the separate hub portion. For example, with reference to FIG. 1B, the hub 30 may be formed with only the second hub portion 34 and the side port 38 attached to the hub arm 36. The valve body 52 may be secured to the first end 34a of the second hub portion 34, e.g., by bonding with adhesive, welding or fusing, one or more connectors, and the like. The first hub portion 32 may then be attached to the hub 30 and/or the valve 50. For example, the first hub portion 32 may be attached to the first end 36a of the hub arm 36, e.g., using the methods described above, and the second end 32b of the first hub portion 32 may be attached to the valve body 52, e.g., similar to the second hub portion 34.

Figure 7A:
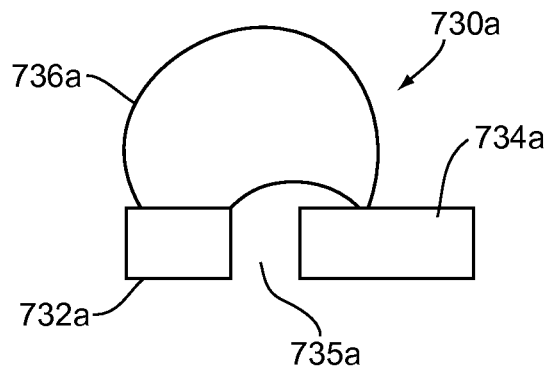
FIGS. 7A-7C are side views of alternative embodiments of handles that may be provided for receiving a valve.

Turning to FIG. 7A, an alternative embodiment of a hub 730a is shown that includes a first hub portion 732a integrally formed with or otherwise attached to a hub arm 736a. A separate second hub portion 734a may be formed that may be attached to the hub arm 736a after a valve (not shown) has been attached to one or both hub portions 732a, 734a.

Figure 7B:
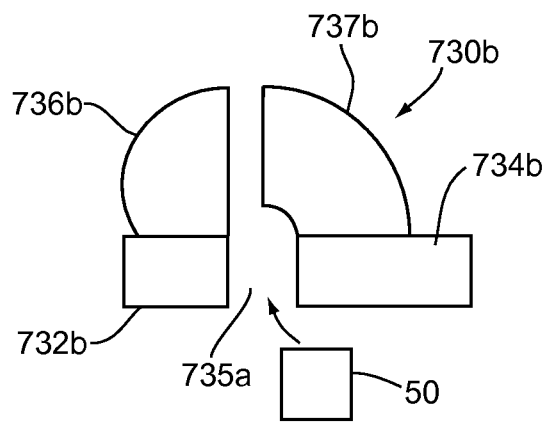
Figure 7C:
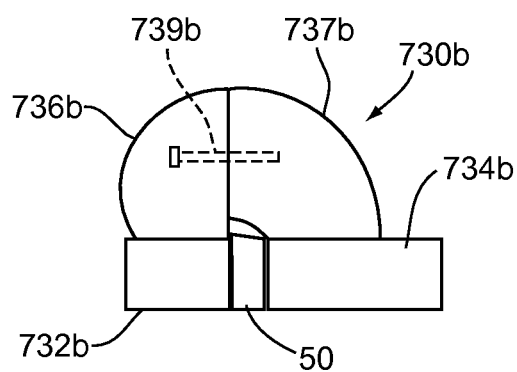

Turning to FIGS. 7B and 7C, yet another alternative embodiment of a hub 730b is shown that includes a first hub portion 732b integrally formed with or attached to a first handle portion 736b and a second hub portion 734b integrally formed with or attached to a second handle portion 737b, as shown in FIG. 7B. When the handle portions 736b, 737b are placed together, as shown in FIG. 7C, a gap 735b remains between the hub portions 732b, 734b for receiving a valve 50, similar to other embodiments herein. Thus, when a valve 50 is secured to one or both of the hub portions 732b, 734b, the handle portions 736b, 737b may be attached together, e.g., using one or more fasteners 739b, e.g., screws, bolts, pins, rivets, and the like, as shown. In addition or alternatively, the handle portions 736b, 737b may be attached together by bonding with adhesive, fusing, sonic welding, cooperating detents or other connectors, and the like (not shown).

Once the valve 50 is secured or otherwise captured within the gap 35 of the hub 30, the hub 30 (which may be any of the embodiments herein) may be incorporated into an apparatus 10, as shown in FIG. 1A. For example, the second end 34b of the second hub portion 34 may be attached to the proximal end 12 of the tubular body 11, e.g., after (or optionally before) assembling the hub 30. The resulting apparatus 10 may be sterilized and/or packaged, as desired, and provide to a user, or the apparatus 10 without the valve 50 may be provided to a user for assembly immediately before a procedure, e.g., as described above.

During use, the apparatus 10 may be used for delivering a medical device into a body lumen within a patient's body, e.g., a lead, catheter, and the like, into a patient's vasculature or other body lumen, as described above. For example, a distal end 14 of the tubular body 11 may be introduced into a patient's vasculature with the hub 30 and valve 50 remaining outside the patient's body. The tubular body 11 may be advanced through the patient's vasculature, e.g., to position the distal end 14 and a desired location, e.g., a coronary vein within the patient's heart or other body lumen. A medical device, e.g., a pacing or other electrical lead, a guidewire, and/or other instrument (not shown), may be inserted through the first hub portion 32, the valve 50, and the second hub portion 34 and into the tubular body 11 until a distal end of the medical device is advanced into the body lumen, e.g., exiting or remaining within the distal end 14 of the tubular body 11.

The apparatus 10 may then be removed to leave the medical device implanted within the patient's body. The configuration of the hub 30 may facilitate removing the apparatus 10 from around the medical device without substantial risk of dislodging or otherwise moving the medical device. For example, cardiac leads often include relatively large proximal hubs, e.g., including electrical connectors and the like, which may prevent the apparatus 10 from being removed over the hub. Instead, a slitter or other tool (not shown) may be used to slit the hub 30, valve, and tubular body 11 to open the apparatus 10 and allow easy removal despite a large hub or other obstacle.

For example, a slitter may be used sequentially cut the first hub portion 32, the valve body 52, the second hub portion 34, and the tubular body 11. If the hub portions 32, 34 and/or valve body 52 include relatively thin walled regions aligned with one another, the regions may be identified, e.g., by a colored line, a recess (not shown) in the first end 32a of the first hub portion 32, and the like, to facilitate identification by the user. Optionally, the tubular body 11 may include a tearaway or other weakened region that may be aligned with the relatively thin walled regions of the hub 30, which may facilitate slitting or may simply propagate separation of the region along the length of the tubular body 11 with or without use of a slitter or other tool.

Because the valve body 52 is slit separately from the hub portions 32, 34, the user only needs to slit one layer of material, which may facilitate slitting the hub 30, e.g., compared to hubs with valves disposed concentrically within a tubular hub. Simultaneously slitting such a concentric valve and tubular hub may require greater force, since multiple layers of dissimilar materials must be slit together, which increases the risk of moving the medical device being implanted, as explained in the applications incorporated by reference elsewhere herein.

With reference to FIGS. 2A-2C, another advantage of the valves described herein is that the valve body 52 may have an overall length that is substantially shorter than conventional valves. This relatively short length may reduce friction between the valve 50 and medical device inserted through the valve passage 60 since there is less surface area to contact the medical device. This is particularly useful when the valve body 52 is formed from materials, such as silicone, which may be tacky.

With further reference to FIGS. 2A-2C, still another advantage of the valve 50 described herein is that the recess 69 at the bottom of the bore 62 within the valve body 52 may limit propagation of a tear when a medical device is inserted through the valve passage 60 of the valve 50. For example, if a medical device is inserted through the bore 62 into the slit 64 and causes the slit 64 to tear further into the valve body 52, the recess 69 may provide a negative cavity creating a "rip stop" that may prevent the tear from propagating towards the first end 54 of the valve body 52. If the valve body 52 surrounding the bore 62 were to tear, there would be substantially increased risk of leaking around the medical device inserted through the valve passage 60. Similarly, any tear that is created by over-expansion of the bore 62 may be prevented from propagating towards the valve body 52 surrounding the slit 64 due to the rip stop provided by the recess 69.

With further reference to FIGS. 2A-2C, still another advantage of valves described herein is that because such valves are not disposed concentrically within a tubular hub, they may expand unconstrained to accommodate insertion of a medical device. As a result, the valve 50, including the bore 62, may be sized to seal on a relatively small device, such as a guidewire, while accommodating passage of a relatively larger device, such as a lead or catheter, without causing excessive friction during passage of the relatively larger device.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A valve for a hub of a sheath, catheter, or other tubular device, comprising:
    a valve body comprising an inlet end, an outlet end, a central longitudinal axis extending between the inlet and outlet ends, and an outer surface extending from the outlet end at least partially towards the inlet end;
    a bore extending partially through the valve body from the inlet end towards the outlet end; and
    a slit extending transversely through the valve body from a first side of the outer surface partially towards an opposite second side of the outer surface, thereby defining a cover in the valve body located between the bore and the outlet end, the cover biased to close the bore and resiliently flexible to open to accommodate an instrument introduced through the bore from the inlet end,
    wherein the valve body includes a pair of stops extending from the outer surface adjacent the second side for supporting the cover adjacent a base of the slit, and wherein the stops include stop surfaces defining an acute angle with the outer surface adjacent the base of the slit such that the stops resist propagation of the slit to the second side of the outer surface.

2. The valve of claim 1, wherein the bore extends substantially parallel to the central axis from the inlet end partially towards the outlet end.

3. The valve of claim 1, wherein the bore defines a bore axis that is substantially parallel to and offset from the central axis such that one side of the bore is closer to the outer surface of the valve body than the opposite side of the bore.

4. The valve of claim 1, further comprising:
    a substantially planar valve support extending radially outwardly from the valve body; and
    a pair of annular flanged connectors extending from an outer portion of the valve support substantially parallel to the central axis, the flanged connectors sized for being received over spaced apart hub portions of a hub for supporting the valve body between the hub portions.

5. The valve of claim 4, wherein the flanged connectors include opposite ends spaced apart from one another, the flanged connectors including relatively thin-walled regions between the valve support and the opposite ends to enhance flexibility of the flanged connectors.

6. A valve for a hub of a sheath, catheter, or other tubular device, comprising:
    a valve body comprising an inlet end, an outlet end, a central longitudinal axis extending between the inlet and outlet ends, and an outer surface extending from the outlet end at least partially towards the inlet end;

a bore extending partially through the valve body from the inlet end towards the outlet end; and a slit extending transversely through the valve body from a first side of the outer surface partially towards an opposite second side of the outer surface, thereby defining a cover in the valve body located between the bore and the outlet end, the cover biased to close the bore and resiliently flexible to open to accommodate an instrument introduced through the bore from the inlet end, wherein the valve body includes a pair of stops extending from the outer surface adjacent the second side for supporting the cover adjacent a base of the slit, and a substantially planar valve support extending radially outwardly from the valve body;

a pair of annular flanged connectors extending from an outer portion of the valve support substantially parallel to the central axis, the flanged connectors sized for being received over spaced apart hub portions of a hub for supporting the valve body between the hub portions;

wherein the flanged connectors include opposite ends spaced apart from one another, the flanged connectors including relatively thin-walled regions between the valve support and the opposite ends to enhance flexibility of the flanged connectors, and wherein the thin-walled regions define annular recesses on inner surfaces of the flanged connectors adjacent the valve support sized for receiving adhesive therein to enhance securing the flanged connectors to the hub portions.

7. The valve of claim 1, wherein the valve body includes a transition from the inlet end to the bore for guiding an instrument into the bore from the inlet end.

8. A valve for a hub of a sheath, catheter, or other tubular device, comprising:

a valve body comprising an inlet end, an outlet end, a central longitudinal axis extending between the inlet and outlet ends, and an outer surface extending from the outlet end at least partially towards the inlet end;

a bore extending partially through the valve body from the inlet end towards the outlet end; and a slit extending transversely through the valve body from a first side of the outer surface partially towards an opposite second side of the outer surface, thereby defining a cover in the valve body located between the bore and the outlet end, the cover biased to close the bore and resiliently flexible to open to accommodate an instrument introduced through the bore from the inlet end, wherein the valve body includes a pair of stops extending from the outer surface adjacent the second side for supporting the cover adjacent a base of the slit, wherein the valve body includes a transition from the inlet end to the bore for guiding an instrument into the bore from the inlet end, and wherein the bore defines a substantially uniform diameter passage extending from the inlet end partially through the valve body, the transition comprising a recess surrounding the passage extending from the inlet end partially through the valve body a shorter distance than the passage.

9. A valve for a hub of a sheath, catheter, or other tubular device, comprising:

a valve body comprising an inlet end, an outlet end, a central longitudinal axis extending between the inlet and outlet ends, and an outer surface extending from the outlet end at least partially towards the inlet end;

a bore extending partially through the valve body from the inlet end towards the outlet end; and a slit extending transversely through the valve body from a first side of the outer surface partially towards an opposite second side of the outer surface, thereby defining a cover in the valve body located between the bore and the outlet end, the cover biased to close the bore and resiliently flexible to open to accommodate an instrument introduced through the bore from the inlet end, wherein the valve body includes a pair of stops extending from the outer surface adjacent the second side for supporting the cover adjacent a base of the slit, and wherein the outer surface of the valve body defines a first curved surface extending circumferentially from the second side partially around the valve body towards the first side, the stops comprising supports extending radially outwardly from the first curved surface to provide stop surfaces defining an acute angle between each stop surface and the first curved surface.

10. A valve for a hub of a sheath, catheter, or other tubular device, comprising:

a valve body comprising an inlet end, an outlet end, a central longitudinal axis extending between the inlet and outlet ends, a bore extending partially through the valve body from the inlet end towards the outlet end, and a slit at least partially defining a self-closing feature between the bore and the outlet end, the self-closing feature biased to close to substantially seal the bore and resiliently flexible to open to accommodate an instrument introduced through the bore from the inlet end; and a pair of annular flanged connectors extending substantially parallel to the central axis and surrounding the valve body, the flanged connectors sized for being received over spaced apart hub portions of a hub for supporting the valve body in a gap between the hub portions, wherein the valve body includes a pair of stops extending from the outer surface adjacent the second side for supporting the cover adjacent a base of the slit, and wherein the stops include stop surfaces defining an acute angle with the outer surface adjacent the base of the slit such that the stops resist propagation of the slit to the second side of the outer surface.

11. The valve of claim 10, wherein the valve body comprises an outer surface extending from the outlet end at least partially towards the inlet end, and wherein the slit extends transversely through the valve body from a first side of the outer surface partially towards an opposite second side of the outer surface, the self-closing feature comprising a cover at least partially defined by the slit, the cover biased to close the bore and resiliently flexible to open to accommodate an instrument introduced through the bore from the inlet end.

12. The valve of claim 11, further comprising a valve support extending radially outwardly from the valve body, the flanged connectors extending from an outer region of the valve support.

13. The valve of claim 10, wherein the slit extends substantially parallel to the central axis through the valve body from the bore to the outlet end, the self-closing feature comprising opposing slit regions at least partially defined by the slit that open to accommodate receiving an instrument through the bore yet resiliently close when the instrument is removed to maintain a substantially fluid tight seal.

14. The valve of claim 10, wherein the flanged connectors include opposite ends spaced apart from one another, the flanged connectors including relatively thin-walled regions between the valve support and the opposite ends to enhance flexibility of the flanged connectors.

15. The valve of claim 10, wherein the valve body, valve support, and flanged connectors are integrally formed from a single body of material.

16. A valve for a hub of a sheath, catheter, or other tubular device, comprising:
- a valve body comprising an inlet end, an outlet end, a central longitudinal axis extending between the inlet and outlet ends, and an outer surface extending from the outlet end at least partially towards the inlet end;
- a bore extending partially through the valve body from the inlet end towards the outlet end; and
- a slit extending transversely through the valve body from a first side of the outer surface partially towards an opposite second side of the outer surface, thereby defining a cover in the valve body located between the bore and the outlet end, the cover biased to close the bore and resiliently flexible to open to accommodate an instrument introduced through the bore from the inlet end,
- wherein the valve body includes a pair of stops extending from the outer surface adjacent the second side for supporting the cover adjacent a base of the slit, and
- wherein the bore comprises a bottom surface spaced apart from the outlet end, the valve body further comprising a recess adjacent the bottom surface that has a larger cross-section than the bore.

17. The valve of claim 16, further comprising a lubricant within the recess to reduce friction when an instrument is inserted through the bore.

18. The valve of claim 1, wherein the valve body is resiliently flexible such that the cover may resiliently bend or fold away from the bore to accommodate receiving an instrument through the bore and the valve body from the inlet end out the outlet end, the cover resiliently returning towards the bore when the instrument is removed to maintain a substantially fluid tight seal through the bore.

* * * * *